United States Patent
Lin et al.

(10) Patent No.: US 11,929,177 B2
(45) Date of Patent: Mar. 12, 2024

(54) ADAPTIVE PAIN MANAGEMENT AND REDUCTION BASED ON MONITORING USER CONDITIONS

(71) Applicant: International Business Machines Corporation, Armonk, NY (US)

(72) Inventors: Qinghuang Lin, Yorktown Heights, NY (US); Jeffrey L. Rogers, Briarcliff Manor, NY (US); Giovanni Russo, Dublin (IE); Andrea Simonetto, Leixlip (IE); Tigran Tigran Tchrakian, Castleknock (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 457 days.

(21) Appl. No.: 17/224,746

(22) Filed: Apr. 7, 2021

(65) Prior Publication Data
US 2021/0225514 A1    Jul. 22, 2021

Related U.S. Application Data

(63) Continuation of application No. 15/986,409, filed on May 22, 2018, now Pat. No. 11,004,563.

(51) Int. Cl.
*G16H 50/20* (2018.01)
*G16H 50/50* (2018.01)

(52) U.S. Cl.
CPC ............. *G16H 50/20* (2018.01); *G16H 50/50* (2018.01)

(58) Field of Classification Search
CPC ................ G16H 50/20; G16H 50/50
(Continued)

(56) References Cited

U.S. PATENT DOCUMENTS

| 5,908,383 A | 6/1999 | Brynjestad |
|---|---|---|
| 6,249,809 B1 | 6/2001 | Bro |

(Continued)

FOREIGN PATENT DOCUMENTS

| CN | 102314558 A | 1/2012 |
|---|---|---|
| CN | 105844112 A | 8/2016 |

OTHER PUBLICATIONS

Non Final Office Action received for U.S. Appl. No. 15/986,617 dated May 25, 2022, 54 pages.
(Continued)

*Primary Examiner* — Michael Tomaszewski
(74) *Attorney, Agent, or Firm* — Amin, Turocy & Watson, LLP

(57) ABSTRACT

Techniques regarding pain treatment are provided. For example, one or more embodiments described herein can comprise a system, which can comprise a memory that can store computer executable components. The system can also comprise a processor, operably coupled to the memory, and that can execute the computer executable components stored in the memory. The computer executable components can include: a data collection component that can determine at least one parameter associated with a pain perception of a subject, a computing component that can determine a relationship between the pain perception and the at least one parameter using artificial intelligence, and can determine a treatment for the subject based on the relationship; and a treatment component that can cause a device associated with the subject to apply at least a portion of the treatment.

20 Claims, 10 Drawing Sheets

(58) Field of Classification Search
USPC .................................................... 705/2–3
See application file for complete search history.

(56) References Cited

U.S. PATENT DOCUMENTS

| | | | |
|---|---|---|---|
| 7,229,430 B2 | 6/2007 | Hickle et al. | |
| 7,251,609 B1 | 7/2007 | McAlindon et al. | |
| 7,463,927 B1 | 12/2008 | Chaouat | |
| 7,596,410 B1* | 9/2009 | Kroll .................. | A61N 1/39624 |
| | | | 607/14 |
| 7,801,591 B1* | 9/2010 | Shusterman .......... | G16H 50/20 |
| | | | 600/509 |
| 7,957,809 B2 | 6/2011 | Bourget et al. | |
| 8,046,241 B1 | 10/2011 | Dodson | |
| 8,086,563 B2 | 12/2011 | Jung et al. | |
| 8,380,314 B2 | 2/2013 | Panken et al. | |
| 8,380,531 B2 | 2/2013 | Paty et al. | |
| 8,469,713 B2 | 6/2013 | Kron et al. | |
| 8,636,273 B2 | 1/2014 | Saito | |
| 9,147,041 B2 | 9/2015 | Amarasingham et al. | |
| 9,262,688 B1 | 2/2016 | Zadeh | |
| 9,536,049 B2 | 1/2017 | Brown et al. | |
| 9,782,122 B1 | 10/2017 | Pulliam et al. | |
| 2001/0012913 A1 | 8/2001 | Iliff | |
| 2002/0128866 A1 | 9/2002 | Goetzke et al. | |
| 2003/0178031 A1 | 9/2003 | Du Pen et al. | |
| 2004/0064709 A1 | 4/2004 | Heath | |
| 2006/0265023 A1* | 11/2006 | Blumberg ............... | A61F 11/12 |
| | | | 607/46 |
| 2006/0293572 A1 | 12/2006 | Bulat | |
| 2007/0032827 A1* | 2/2007 | Katims ................ | A61N 1/3787 |
| | | | 607/46 |
| 2007/0239484 A1* | 10/2007 | Arond ................ | G06Q 10/0637 |
| | | | 705/2 |
| 2007/0271272 A1 | 11/2007 | McGuire et al. | |
| 2008/0059241 A1 | 3/2008 | Zahlmann et al. | |
| 2009/0157141 A1 | 6/2009 | Chiao et al. | |
| 2010/0087795 A1 | 4/2010 | Krijnsen et al. | |
| 2010/0153832 A1 | 6/2010 | Markus et al. | |
| 2011/0035158 A1 | 2/2011 | Banos et al. | |
| 2011/0054564 A1 | 3/2011 | Valencia | |
| 2012/0078837 A1 | 3/2012 | Bagchi et al. | |
| 2012/0316898 A1 | 12/2012 | Levitt et al. | |
| 2013/0173277 A1 | 7/2013 | Eller et al. | |
| 2013/0244336 A1 | 9/2013 | Mayer et al. | |
| 2013/0296987 A1* | 11/2013 | Rogers ...................... | A61F 7/12 |
| | | | 607/113 |
| 2014/0074454 A1 | 3/2014 | Brown et al. | |
| 2014/0074509 A1 | 3/2014 | Amarasingham et al. | |
| 2014/0108034 A1* | 4/2014 | Akbay ............. | G06Q 10/06315 |
| | | | 705/2 |
| 2014/0275827 A1 | 9/2014 | Gill et al. | |
| 2014/0276188 A1* | 9/2014 | Jardin .................. | A61B 5/7267 |
| | | | 600/544 |
| 2014/0276549 A1* | 9/2014 | Osorio ................... | A61B 5/165 |
| | | | 604/503 |
| 2014/0316793 A1 | 10/2014 | Pruit | |
| 2015/0019241 A1 | 1/2015 | Bennett et al. | |
| 2015/0193583 A1 | 7/2015 | McNair et al. | |
| 2015/0199484 A1 | 7/2015 | Morris et al. | |
| 2015/0254408 A1 | 9/2015 | Dadlani Mahtani et al. | |
| 2015/0278474 A1 | 10/2015 | Stueckemann et al. | |
| 2015/0287330 A1 | 10/2015 | Kron et al. | |
| 2016/0030281 A1* | 2/2016 | Shafieloo ........... | A61H 23/0245 |
| | | | 601/48 |
| 2016/0051434 A1* | 2/2016 | Erkiliç ................. | A61H 1/0274 |
| | | | 601/26 |
| 2016/0100790 A1 | 4/2016 | Cantu et al. | |
| 2016/0117484 A1 | 4/2016 | Hanina et al. | |
| 2016/0198996 A1 | 7/2016 | Dullen | |
| 2016/0210424 A1 | 7/2016 | Di Battista | |
| 2016/0213314 A1 | 7/2016 | Zuckerman-Stark et al. | |
| 2016/0335412 A1 | 11/2016 | Tucker et al. | |
| 2016/0339241 A1 | 11/2016 | Hargrove et al. | |
| 2017/0004260 A1 | 1/2017 | Moturu et al. | |
| 2017/0056642 A1 | 3/2017 | Moffitt et al. | |
| 2017/0124269 A1 | 5/2017 | McNair et al. | |
| 2018/0018966 A1 | 1/2018 | Leonard | |
| 2018/0039763 A1 | 2/2018 | Tidor | |
| 2018/0133101 A1* | 5/2018 | Inada .................. | A61H 23/02 |
| 2018/0278554 A1 | 9/2018 | Kassabgi | |
| 2018/0307678 A1 | 10/2018 | Anantaram et al. | |
| 2019/0065970 A1* | 2/2019 | Bonutti ................ | G06T 7/0012 |
| 2019/0140986 A1 | 5/2019 | Anderson et al. | |
| 2019/0192874 A1* | 6/2019 | Shukla ................... | A61N 2/02 |
| 2019/0275270 A1* | 9/2019 | Postrel ................ | A61K 31/352 |

OTHER PUBLICATIONS

Baliki, et al., Corticostrialal functional connectivity predicts transition to chronic back pain, Nat Neurosci., Jul. 1, 2012; 15(8): 1117-9, doi: 10.1038/nn.3153.
Notice of Allowance received for U.S. Appl. No. 17/135,304 dated Feb. 10, 2023, 23 pages.
Notice of Allowance received for U.S. Appl. No. 17/134,686 dated Feb. 1, 2023, 23 pages.
Notice of Allowance received for U.S. Appl. No. 17/134,954 dated Feb. 10, 2023, 24 pages.
Non Final Office Action received for U.S. Appl. No. 17/135,304 dated Oct. 14, 2022, 41 pages.
Non Final Office Action received for U.S. Appl. No. 17/134,686 dated Sep. 29, 2022, 44 pages.
Non Final Office Action received for U.S. Appl. No. 17/134,954 dated Oct. 14, 2022, 45 pages.
Non-Final Office Action received for U.S. Appl. No. 15/986,564 dated May 4, 2021, 61 pages.
Non-Final Office Action received for U.S. Appl. No. 15/986,409 dated Jun. 25, 2020, 38 pages.
Baker, et al., Experience and knowledge of pain management in patients receiving outpatient cancer treatment: What do older adults really know about their cancer pain?, Pain Medicine, 2014, pp. 52-60, vol. 15. No. 1.
Hallenbeck, Pain and Intercultural Communication, Handbook of Pain and Palliative Care, Chapter 2, 2013, 24 Pages.
Pinto, et al., Patient-centred communication is associated with positive therapeutic alliance: a systematic review, Journal of Physiotherapy, 2012, pp. 77-87. vol. 58.
Anonymous, Method and System for Enhanced Medication Management System, Nov. 25, 2016, 5 Pages.
Kalia, et al., Goven: estimating trust from communications, Journal of Trust Management, 2016, 19 Pages, vol. 3, No. 1.
Anonymous, Methods & devices for managing and monitoring arthritis patients, IP.com No. IPCOM000247325D; Aug. 23, 2016, 7 pages.
Temple, Enrichment Strategies for Clinical Trials, CDER Enrichment Webinar, Mar. 25, 2013, 40 Pages.
Victor, et al., Trustworthiness as a Clinical Variable: The Problem of Trust in the Management of Chronic, Nonmalignant Pain, Pain Medicine, 2005, pp. 385-391, vol. 6, No. 5.
Buchman, et al., You Present like a Drug Addict: Patient and Clinician Perspectives on Trust and Trustworthiness in Chronic Pain Management, Pain Medicine, 2016, pp. 1394-1406, vol. 17.
Castle, et al., Neural and behavioral bases of age differences in perceptions of trust, PNAS, Dec. 12, 2012, pp. 20848-20852, vol. 109, No. 51.
Baliki, et al., Brain Morphological Signatures for Chronic Pain, PLoS One, Oct. 13, 2011, 13 Pages, vol. 6, No. 10.
Eickhoff, et al., Functional Segregation of the Human Dorsomedial Prefrontal Cortex, Cerebral Cortex, Jan. 2016, pp. 304-321, vol. 26.
Hashmi, et al., Shape shifting pain: chronification of back pain shifts brain representation from nociceptive to emotional circuits, Brain A Journal of Neurology, Jun. 14, 2013, pp. 2751-2768, vol. 136.
Fett, et al., Social neuroscience in psychiatry: unravelling the neural mechanisms of social dysfunction, Psychological Medicine, Sep. 18, 2014, 21 Pages.

(56) References Cited

OTHER PUBLICATIONS

Tsukiura, et al., Insular and hippocampal contributions to remembering people with an impression of bad personality, SCAN, 2013, pp. 515-522, vol. 8.
Vachon-Presseau, et al., Corticolimbic anatomical characteristics predetermine risk for chronic pain, Brain A Journal of Neurology, 2016, pp. 1958-1970, vol. 139.
Getov, et al., Human brain structure predicts individual differences in preconscious evaluation of facial dominance and trustworthiness, SCAN, 2015, pp. 690-699, vol. 10.
Mansour, et al., Brain white matter structural properties predict transition to chronic pain, Pain, Oct. 2013, pp. 2160-2168, vol. 154, No. 10.
Baliki, et al., Corticostrialal functional connectivity predicts transition to chronic back pain, National Neuroscience, pp. 1117-1119, vol. 15, No. 8.
Sprengelmeyer, et al., The neuropsychology of first impressions: Evidence from Huntington's disease, Cortex, Dec. 10, 2016, 41 Pages.
Baliki, et al., Predicting value of pain and analgesia: nucleus accumbens response to noxious stimuli changes in the presence of chronic pain, Neuron, Apr. 15, 2010, pp. 149-160, vol. 66, No. 1.
Tetreault, et al., Brain Connectivity Predicts Placebo Response across Chronic Pain Clinical Trials, PLOS Biology, Oct. 27, 2016, vol. 14, No. 10.
Pecina, et al., Personality Trait Predictors of Placebo Analgesia and Neurobiological Correlates, Neuropsychopharmacology, 2013, pp. 639-646, vol. 38.
Schafer, et al., Health Care Providers' Judgments in Chronic Pan: The Influence of Gender and Trustworthiness, International Association for the Study of Pain, 2016, 32 Pages.
Colloca, et al., Placebo analgesia induced by social observational learning, Pain, Jan. 29, 2009, pp. 28-34, vol. 144.
Geers, et al., Reconsidering the role of personality in placebo effects: Dispositional optimism, situational expectations, and the placebo response, Journal of Psychosomatic Research, 2005, pp. 121-127, vol. 58.
Hyland, et al., Motivational concordance: An important mechanism in self-help therapeutic rituals involving inert (placebo) substances, Journal of Psychosomatic Research, 2008, pp. 405-413, vol. 65.
Tuttle, et al., Increasing placebo responses over lime in U.S. clinical trials of neuropalhic pain, Pain, Dec. 2015, pp. 2616-2626, vol. 156.
Lount, The Impact of Positive Mood on Trust in Interpersonal and Intergroup Interactions, Journal of Personality and Social Psychology, 2010, pp. 420-433, vol. 98, No. 3.
Sessa, et al., Perceived trustworthiness shapes neural empathic responses toward others' pain, Neuropsychologia, 2015, pp. 97-105, vol. 79.
Mel, et al., The NIST Definition of Cloud Computing, National Institute of Standards and Technology Special Publication 800-145, Sep. 2011, 7 Pages.
Mutso et al., "Reorganization of hippocampal functional connectivity with transition to chronic back pain," Journal of Neurophysiology, 2014, pp. 1065-1076, 12 pages.
List of IBM Patents or Applications Treated as Related.
Non-Final Office Action received for U.S. Appl. No. 15/986,579 dated Aug. 6, 2020, 36 pages.
Non-Final Office Action received for U.S. Appl. No. 15/986,566 dated Jul. 24, 2020, 33 pages.
Non-Final Office Action received for U.S. Appl. No. 15/986,598 dated Aug. 7, 2020, 36 pages.
Final Office Action received for U.S. Appl. No. 15/986,409 dated Oct. 2, 2020, 44 pages.
Notice of Allowance received for U.S. Appl. No. 15/986,566 dated Nov. 3, 2020, 25 Pages.
Notice of Allowance received for U.S. Appl. No. 15/986,409 dated Jan. 7, 2021, 44 pages.
Notice of Allowance received for U.S. Appl. No. 17/135,304 dated May 4, 2023, 6 pages.
Notice of Allowance received for U.S. Appl. No. 17/134,954 dated May 4, 2023, 6 pages.

* cited by examiner

ADAPTIVE PAIN MANAGEMENT AND REDUCTION BASED ON MONITORING USER CONDITIONS

PARTIES TO A JOINT RESEARCH AGREEMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

BACKGROUND

One or more embodiments relate to electronic systems in healthcare, and more specifically, to adaptive systems for pain management using artificial intelligence technology.

SUMMARY

The following presents a summary to provide a basic understanding of one or more embodiments of the disclosure. This summary is not intended to identify key or critical elements, or to delineate any scope of particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can autonomously provide pain treatments based on human subjects and environmental conditions measured and analyzed using artificial intelligence technology are described.

According to an embodiment, a system is provided. The system can comprise a memory that stores computer executable components. The system can also comprise a processor, operably coupled to the memory, and that can execute the computer executable components stored in the memory. The computer executable components can comprise: a computing component that determines a relationship between a pain perception of a subject and at least one parameter using artificial intelligence, and determines a treatment to reduce pain perception for the subject based on the relationship; and a communication component that transfers information between at least two of a data collection component, the computing component, the communication component, and a treatment component, the information associated with one or more of the at least one parameter, the relationship, or the treatment.

According to one or more example embodiments, a computer-implemented method is provided. The computer-implemented method comprises: determining, by a data collection component, at least one parameter associated with a pain perception of a user. The computer-implemented method further comprises determining, by a computing component operatively coupled to the processor, a relationship between a pain perception of a subject and at least one parameter using artificial intelligence; determining, by the computing component, a treatment to reduce pain perception for the subject based on the relationship; and transferring, by a communication component operatively coupled to the processor, information between at least two of a data collection component, the computing component, the communication component, and the treatment component, the information associated with one or more of the at least one parameter, the relationship, or the treatment.

According to yet one or more example embodiments, a computer program product is provided. The computer program product can comprise a computer readable storage medium having program instructions embodied therewith. The program instructions can be executable by a processor to cause the processor to determine, by the processor, a relationship between a pain perception of a subject and at least one parameter using artificial intelligence; and determine, by the processor, a treatment to reduce pain perception for the subject based on the relationship, the treatment including an implantable device that provides medication delivery to the subject.

DETAILED DESCRIPTION

Figure 1:
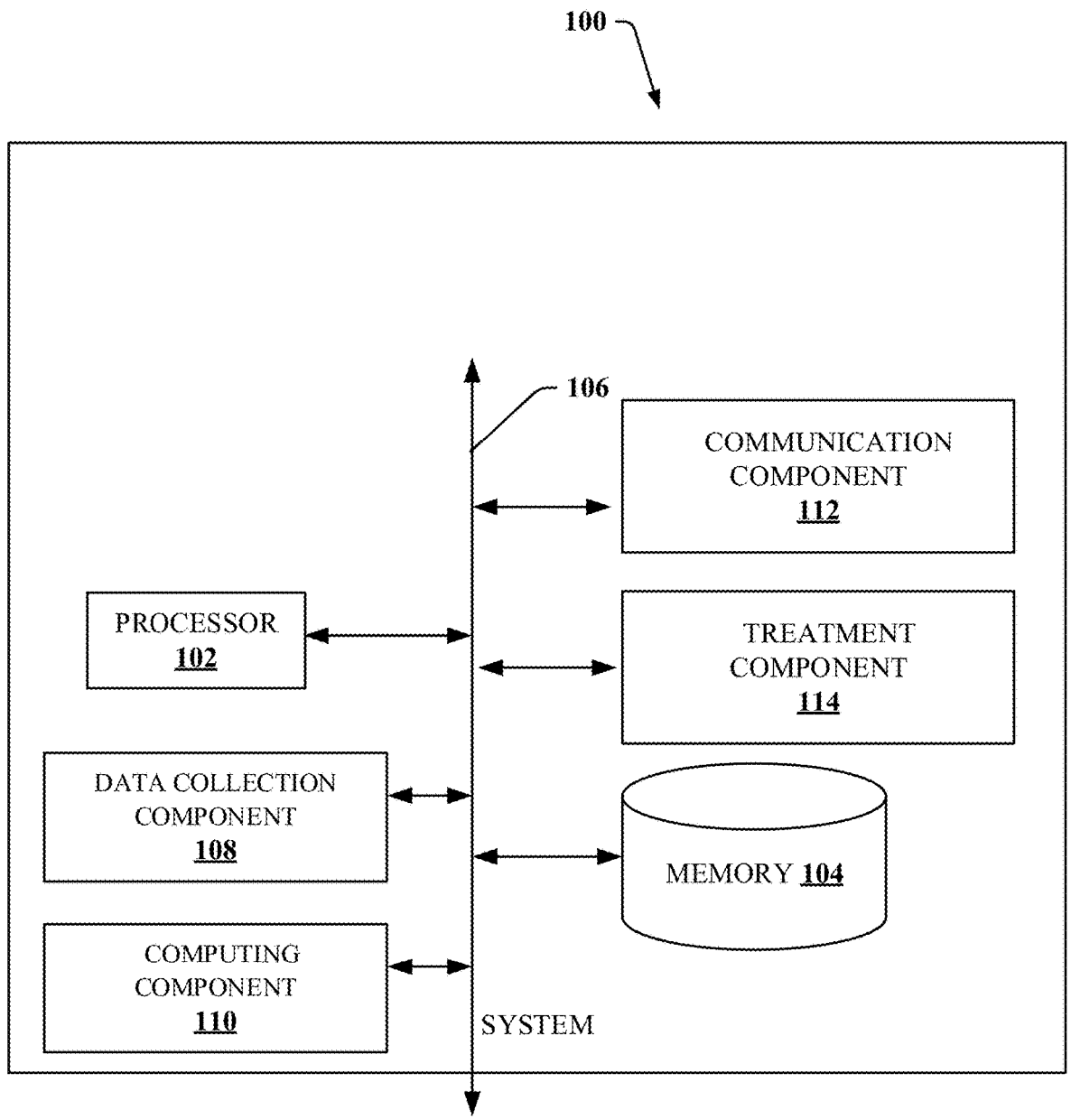
FIG. 1 illustrates a block diagram of an example, non-limiting system for the mitigation and management of pain perception of a human subject, in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

It is to be understood that although this disclosure includes a detailed description on cloud computing, implementation of the teachings recited herein are not limited to a cloud computing environment. Rather, embodiments of the present disclosure are capable of being implemented in conjunction with any other type of computing environment now known or later developed.

Personalized healthcare represents a development in the field of healthcare that seeks to leverage Internet-of-Things (IoT) devices to deliver individualized treatments to users.

However, there remain many challenges in integrating Internet-of-things (IoT) devices with personalized healthcare. Leveraging quantitative analytics in personalized healthcare can enable the development of adaptive systems that model embodiments of patient health for integration with IoT devices.

Typical treatments for relieving and/or managing pain in patients may not account for external parameters and user feedback when making treatment recommendations. Such treatments may, for example, give full control to a user in deciding a stimulus to be applied to themselves via a user device. An example of such a user device can include an electrode to transmit electromagnetic radiation to a region of the user's body experiencing pain. The user may decide on the stimulus without a further analysis, by the system, of the user's condition (e.g., a user's temperature, physiological or psychological state, and the like). In another example, the treatments may merely involve providing a prescription medication or patch (e.g., transdermal patch) for treating the pain. However, no further analysis of contextual elements such as user behaviors and/or environmental factors may be considered when determining treatments or updated treatments. Accordingly, such typical pain relief treatments may inadvertently cause the users to suffer more than necessary. Further, typical pain relief systems and methods may choose only a subset of several possible treatments, such as medication, instead of a combination of different treatments, such as a combination of medication, electromagnetic stimulation in addition to massages or specific exercises.

In various embodiments, the disclosure is generally directed to providing personalized treatment for pain mitigation using artificial intelligence (AI). In some embodiments, the disclosure can facilitate the application of treatments. Further, the treatments can be adapted and modified in real-time, for example, based on the psychological and/or physiological state of the users and on one or environmental conditions associated with the users. Examples of pain that can be treated in accordance with the disclosure can include, but not be limited to, headaches, migraines, menstrual cramps, minor trauma (such as a bruise, abrasions, sprains), severe trauma (such as a wound, burn, bone fracture, or severe sprain, strain or pulled muscle), pain after surgery, muscle aches, toothaches or pain from dental procedures, kidney stone pains, pain due to heartburn or gastroesophageal reflux disease, chronic back pain, osteoarthritis pain, fibromyalgia, and the like.

In various embodiments, treatments that can be implemented in accordance with the disclosure can include, but not be limited to, pulsed radiofrequency, neuromodulation, direct introduction of medication and nerve ablation targeting either tissue structures and organ/systems responsible for pain perception. Treatments can further include epidural steroid injections, facet joint injections, neurolytic blocks, spinal cord stimulation and intrathecal medication delivery systems. Treatments may include an intrathecal pump that can be used to deliver small quantities of medications directly to particular body structures, for example, the spinal fluid. Examples of non-invasive therapies that may be recommended by the systems described herein can include, but not be limited to, cognitive behavioral therapy (CBT), hypnosis, and/or mindful meditation. CBT can refer to treatments that allows patients with pain to understand the relationship between one's physiology (e.g., pain and muscle tension), thoughts, emotions, and behaviors. The treatment can include cognitive restructuring to encourage helpful thought patterns, targeting a behavioral activation of healthy activities such as regular exercise and pacing. In some embodiments, lifestyle changes may also be recommended to improve sleep patterns and to develop better coping skills for pain and other stressors using various techniques (e.g., relaxation, breathing techniques, and biofeedback).

In one embodiment, the treatment can include electrical stimulation for pain management without using any implantable devices, e.g., electrical stimulation provided by a contact or non-contact patch on or near the surface of the body of the subject. For example, a contact patch can apply electrical simulation via electric currents that are passed through a gel-like electrode that is affixed to a portion of the body. A non-contact patch can send electromagnetic radiation of given amplitude, frequency, and phase (e.g., using hypothermia methods) through the atmosphere toward the portion of the body to alleviate pain. In another embodiment, the treatment for pain management can include an implantable device providing treatments other than electrical stimulation, e.g., a medication-delivery implantable device, an implantable device configured to apply radiation (such as ultraviolet radiation, light, and/or heat) to portion of the body, an implantable device configured to apply a force or pressure to a portion of the body (e.g., to massage a portion of the body), an implantable device configured to apply ultrasound to a portion of the body, combinations thereof, and/or the like.

The claims and scope of the subject application, and any continuation, divisional or continuation-in-part applications claiming priority to the subject application, exclude embodiments (e.g., systems, apparatus, methodologies, computer program products and computer readable storage media) directed to implanted electrical stimulation for pain treatment and/or management.

FIG. 1 illustrates a block diagram of an example, non-limiting system 100 for the mitigation and management of pain, in accordance with one or more embodiments described herein. Aspects of systems (e.g., system 100 and the like), apparatuses or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described. Repetitive description of like elements employed in one or more embodiments described herein is omitted for sake of brevity.

System 100 can optionally include a server device, one or more networks and one or more devices (not shown). The system 100 can also include or otherwise be associated with at least one processor 102 that executes computer executable components stored in memory 104. The system 100 can further include a system bus 106 that can couple various components including, but not limited to, a data collection component 108, a computing component 110, a communication component 112, and a treatment component 114. The system 100 can be any suitable computing device or set of computing devices that can be communicatively coupled to devices, non-limiting examples of which can include, but are not limited to, a server computer, a computer, a mobile computer, a mainframe computer, an automated testing system, a network storage device, a communication device, a web server device, a network switching device, a network routing device, a gateway device, a network hub device, a network bridge device, a control system, or any other suitable computing device. A device can be any device that can communicate information with the system 100 and/or any other suitable device that can employ information provided by system 100. It is to be appreciated that system 100, components, models or devices can be equipped with communication component 112 that enable communication between the system, components, models, devices, etc. over one or more networks.

In some embodiments, the system 100 can generate a model that can capture embodiments of pain perception of users and the relationship of such pain perception with one or more treatments. In some embodiments, the system 100 can generate a non-linear dynamical system or model of an arbitrary mathematical order that can relate the treatment to a quantity of interest, for example, a measure of the pain or a variable that correlates with pain (for example, a quality of sleep, a quality of life, an overall satisfaction, and the like associated with user). In some implementations, the data collection component 108 can measure a quantity of interest using one or more sensors or can obtain the quantity of interest via feedback from a user, for example, via a user device (e.g., a mobile phone, a hand-held device, a laptop, or the like). In some embodiments, based on the dynamic system or model, the system 100 can, using the computing component 110, implement a real-time, closed-loop adaptive model that is able to determine and deliver, using the treatment component 114, an optimized treatment for the user. In one or more example embodiments, as the dynamic system or model changes over time, the data collection component 108 can remeasure the quantity of interest, and the computing component 110 can reanalyze the model's parameters. In one embodiment, the model parameters can be taken as input by the system 100 which can adapt in real-time based on the time-evolution of the model's parameters.

In one embodiment, the system 100 described herein can have two modes of operation, a recommender mode of operation and a control mode of operation. In the recommender mode, the system 100 can recommend, using the treatment component 114 and via a user interface, one or more treatments that may be optimal for a user, and allow the user to decide what embodiments of the recommended treatment(s) to apply to themselves. In control mode, the system 100 can automatically deliver a determined treatment to a user using the treatment component 114. The control mode can have an override capability that allows the user to stop the automatic application of the treatment, for example, in case the treatment does not help the user feel better for any reason.

Furthermore, many medicines are typically distributed to patients via a medicine prescription. The medicine prescription is written by a medical professional (e.g., a doctor) and can be taken to a medicine distributor (e.g., a pharmacy) by the patient. The medicine distributor can then distribute one or more medicines to the patient in accordance with the medicine prescription. Similarly, updates to the medicine prescription (e.g., renewals and/or changes in dosage of the medicine) require approval of a medical professional, which typically requires another medical assessment of the patient by the medical professional. For example, medicines having the possibility to cause substantial side effects (e.g., chemical dependency) typically require strict supervision by a medical professional to update associated medicine prescriptions.

Various embodiments of the present disclosure can be directed to computer processing systems, computer-implemented methods, apparatus and/or computer program products that facilitate the generation of a prescription by a medical professional, using artificial intelligence (AI) technology. For example, the system 100 can notify, via the communication component 112, a medical professional that a pain threshold has been exceeded and to therefore prescribe a stronger medication. The treatment unit 114 can further make a recommendation of the prescription based on the dynamic model of pain perception generated for the user.

As used herein, the term "medicine prescription" can refer to an authorization by one or more medical care givers (e.g., medical professionals such as physicians) for an entity to receive one or more medicines and/or medical treatments. Thus, a medicine prescription can authorize distribution of a medicine to an entity. The medicine prescription can delineate one or more features of a subject medicine and/or medical treatment. Example features that can be regarded by a medicine prescription can include but are not limited to: one or more specific medicines to be distributed to the entity, one or more dosages of a subject medicine to be distributed to the entity, a frequency of distribution of a subject medicine and/or dosage to the entity, an amount of medicine to be distributed to an entity, a term of distribution of a medicine to an entity, a combination thereof, and/or the like. For example, a medicine prescription can indicate that an entity is authorized to receive a certain quantity of a specific medicine in a particular dosage at defined frequency (e.g., once). The status of a medicine prescription can regard one or more features of the medicine prescription. Further, an update to the status of a medicine prescription can comprise: changing one or more of the medicine prescription's features (e.g., a change to the frequency of distribution by enabling refills of the medicine prescription), and/or confirming one or more of the medicine prescription's features.

The system 100 can be operatively coupled (e.g., directly and/or indirectly via the one or more networks through use of the communication component 112) to one or more medicine distributors. The one or more medicine distributors can distribute one or more medicines to an entity in accordance with a medicine prescription associated with the user. Example medicine distributors can include, but are not limited to: pharmacies, hospitals, licensed retailers, a combination thereof, and/or the like. In response to updating the status of medicine prescription, the communication component 112 can send (e.g., automatically via the treatment component 114 and/or at the request of a user of the system 100) the updated medicine prescription to the one or more medicine distributors. Alternatively, the one or more medical distributors can maintain one or more prescription databases comprising one or more medicine prescriptions associated with the user; wherein in response to updating the status of medicine prescription the one or more prescription databases can be updated automatically.

The system 100 can be operatively coupled (e.g., directly and/or indirectly via the one or more networks through use of the communication component 112) to one or more medical centers. The one or medical centers can be facilities where medical assistance, medical diagnoses, medical reports, medical therapies, and/or medical treatments can be provided. Example medical centers can include, but are not limited to: hospitals, urgent care clinics, physician practices, nursing homes, a combination thereof, and/or the like. In one or more embodiments, the system can receive, via the communication component 112, medical data from the one or more medical centers. For example, one or more medical professionals (e.g., physicians) at the one or more medical centers can capture images of a subject individual's brain structure to assess one or more neurological features. An individual's brain structure can be indicative of the individual's predisposition to an ailment (e.g., pain and/or chronic pain). The medical data (e.g., one or more brain images and/or medical history) can be sent to the system 100 via the communication component 112 and used to create a treatment via the computing component 110, which can be further augmented based on the other various forms of data described herein.

As used herein, the term "pain" can refer to an unpleasant sensory and/or emotional experience associated with actual or potential tissue damage. Also, as used herein, the term "chronic pain" can refer to pain that persists past a healing period, having widespread effects that can influence one or more levels of a nervous system. Chronic pain can persist for greater than or equal to three months and/or can significantly impact a person's psychological well-being.

One or more ailments (e.g., chronic pain) can be non-stationary over time (e.g., due to a patient's life experiences in combination with their underlying neuropsychological pre-dispositions). Some aliments (e.g., pain) can have dynamic properties such as: varying durations, varying intensities, and/or varying perceived locations. For example, long lasting ailments (e.g., chronic pain) can fluctuate about a mean intensity and/or exhibit peaks in intensity due to external triggers. For instance, neuroimaging can show that dynamics in subjective pain ratings can be reflected in the functional connectivity of sensory and/or emotional brain networks. Also, neurophysiological activity can change as a function of the intensity of pain and/or effectiveness of a medication, even a placebo. Further, a patient's mood can impact the severity of an ailment (e.g., severity of pain) perceived by a patient. Thus, in addition to predisposing factors, one or more ailments (e.g., pain) can produce dynamics that can be tracked in time by the data collection component 108 and linked to internal and/or external perturbations by the computing component 110. Moreover, one or more ailments (e.g., chronic pain) can have temporal, affective, and/or social contexts. For example, both phenomena can increase with age (e.g., older individuals can be more likely to suffer from chronic pain).

In one or more example embodiments, the identification process for determining the system and model that represents the pain perception of the user can be performed in a continuous manner, and model parameters related to the user's condition and/or the user's environment's condition can be updated accordingly. For example, the data collection component 108 can include one or more sensors to gather relevant information, such as a user temperature, vital signs, such as heart rate, respiration rate, an environmental temperature, one or more facial features of the user, a gait or limp associated with the user's movements, sounds (groans, screams, and the like) from the user, and the like. The sensors can include wearable devices such as a smart patch, a smart watch, a smart head band, ingestible device, or infrared sensors, microphones, cameras and associated facial-recognition systems, and the like.

In one or more example embodiments, the uncertainty of the model can also be quantified by the system 100. The uncertainty can be determined automatically; for example, the data collection component 108 can associate a measurement uncertainty with any of the variables measured by the sensors. Non-limiting examples can include an uncertainty in the temperature measurement of a user or a user environment, an uncertainty in the severity of a sound emanated by the user or an association of the sound with a pain, and the like. In other examples, the uncertainty can be based on user feedback at a user device. For example, a user device can ask a question about the user's level of uncertainty in the amount of pain being experienced by the user.

In one or more example embodiments, the treatment component 114 can determine, based on the dynamic model, what an optimal treatment for the user entails, specific for the user's conditions. In one or more example embodiments, the treatment component 114 may not be restricted to choose between a set of pre-determined treatments but can implement machine learning based on a user's past behavior and can generate new treatments accordingly.

In one or more example embodiments, the treatment component 114 can deliver or configure another device to deliver the treatment to the user based on the treatment. For example, the treatment component 114 can send information describing electrical neurostimuli (e.g., magnitude, frequency, waveform type, and the like) to be applied one or more electrodes attached to the user's body. Accordingly, in this embodiment, the treatment can include electrical stimulation for pain management without any implantable devices, e.g., electrical stimulation provided by a contact or non-contact patch on or near the surface of the body of the subject. For example, a contact patch can apply electrical simulation via electric currents that are passed through a gel-like electrode that is affixed to a portion of the body. A non-contact patch can send electromagnetic radiation of given amplitude, frequency, and phase (e.g., using hypothermia methods) through the atmosphere toward the portion of the body to alleviate pain.

In one or more example embodiments, the system 100 can continuously monitor the user to evaluate the effectiveness of the treatment. In one embodiment, the system 100 can adapt the treatment based on the feedback measured from the user. In one or more example embodiments, the treatment can also be adapted in real-time as a function of one or more environmental or user conditions. Examples of such conditions include, but are not be limited to, the user being in a resting state, the user working from home, the outside temperate, and the like. In one or more example embodiments, the user can also directly provide feedback to the system 100, for example, via a user interface. The system 100 can further notify, via the communication component 112, a doctor or medical practitioner of a severity of a pain. In some embodiments, the system 100 can contact a hospital or an emergency system in case the system determines, based on sensor input at the data collection component 108 or based on user feedback that indicates pain exceeding a predetermined threshold, or that the user is not responsive to further treatment.

Embodiments of the disclosure can find application in pain management and therapy involving pharmaceuticals. In such an embodiment, the treatment for pain management can include an implantable device providing treatments other than electrical stimulation, e.g., a medication-delivery implantable device, an implantable device configured to apply radiation (such as ultraviolet radiation, light, and/or heat) to portion of the body, an implantable device configured to apply a force or pressure to a portion of the body (e.g., to massage a portion of the body), an implantable device configured to apply ultrasound to a portion of the body, combinations thereof, and/or the like.

For example, a user may be suffering from severe pain and may be taking pain medication. In this situation, the system 100 can monitor the user in real-time and can determine a dynamic system that models the user's pain perception. In some embodiments, the system 100 can have access (for example, via the data collection component 108 and/or the communication component 112) to information related to the daily activities of the user. Further, the identification process can be continuous the model parameters can be updated accordingly based on the information about the daily activities and the identification process.

In some embodiments, uncertainties associated with one or more parameters of the model can also be quantified. The computing component 110 can determine, based on the model, what combination and timings of pills may minimize pain experienced by the user over a predetermined time window. In one or more example embodiments, the system 100 can function in a recommender mode whereby, once a treatment is determined by the computing component 110, the system can ask the user whether they would consider taking the pills at the dosages and times that are recommended by the system 100. Thereafter, the system 100 can continue to monitor the user to evaluate the effectiveness of the treatment. Based on the feedback measured from the user, the system 100 may recommend, using the computing component 110, an updated combination of type of pills, dosages, and/or pill timing. In some embodiments, the updated suggestion can be a function of one or more environmental and/or user conditions. Examples of such conditions include, but not be limited to, the user being in a resting state, the user working from home, the outside temperate, and the like. In one or more example embodiments, the user can also directly provide feedback to the system 100, for example, via a user interface.

Embodiments of the disclosure can find application in pain management and therapy involving medication-release patches. For example, a user may be suffering from severe pain and may have a prescription medication-release patch attached to the body. In another embodiment, the treatment for pain management can include an implantable device providing treatments other than electrical stimulation, e.g., a medication-delivery implantable device releasing medications into the body or applying medication on the skin.

In some embodiments, the system 100 continuously monitors the user in real-time using the data collection component 108 and computes, using the computing component 110, a specific dynamical system, modelling his/her pain perception. In some embodiments, the system 100 can have access to information related to the daily activities of the user. Further, the identification process can be continuous the model parameters can be updated accordingly based on the information about the daily activities and the identification process.

In some embodiments, uncertainties associated with one or more parameters of the model can also be quantified. The computing component 110 can determine, based on the model, the combination and timing for medication-release that would minimize pain over a certain time interval. The system 100 can operate in a control mode of operation and once a treatment is determined, it can then be delivered to the user. For example, the medication can be released through the patch based on system-provided instructions. Further, based on the feedback from the user, the system 100 may recommend an updated medication-release pattern. In some embodiments, the updated suggestion can be a function of one or more environmental and/or user conditions. Examples of such conditions include, but not be limited to, the user being in a resting state the user working from home, weather conditions, the outside temperate, humidity, and the like. In one or more example embodiments, the user can also directly provide feedback to the system 100, for example, via a user interface.

In various embodiments, components of the system 100 (such as the data collection component 108 and the communication component 112) can include functional elements that can be implemented via cloud technologies, physical components (for example, computer hardware) and local software (for example, an application on a mobile phone or an electronic device).

In some embodiments, the system 100 can include, but not be limited to, the following elements. The data collection component 108 can include sub-systems and apparatuses for real-time data collection, that is, for real-time monitoring of parameters associated with the user and/or the user's behavior, and parameters related to environmental quantities. The data collection component 108 can include one or more sensors. The sensors can include wearable devices such as a smart patch, a smart watch, a smart head band, ingestible device, or infrared sensors, microphones, cameras and associated facial-recognition systems, and the like. The sensors can be used to quantify a physiological condition of a user or an environmental condition.

In some embodiments, the system 100 can include a computing component 110. In some embodiments, the computing component 110 can include a sub-system, method, and/or apparatus to determine a real-time dynamical system for modeling the pain perception for the user. In one or more example embodiments, the dynamical system can be a non-linear dynamical system. In one or more example embodiments, the computing component 110 can serve to determine, based on the dynamical system, a treatment for the user. In one or more example embodiments, the treatment can be optimized for a given user based on the user's immediate psychological, physiological, or environmental conditions. In one or more example embodiments, treatment options can be provided in real-time and be adapted as a function of the user conditions and environmental conditions.

The system 100 can include a treatment component 114. The treatment component 114 can serve to provide a treatment to the user. For example, the treatment component 114 can send one or more electrical pulses to an electrode attached to into the user for the management of pain. The treatment component 114 can facilitate the generation of one or more prescriptions, and make recommendations to a medical practitioner, such as a doctor.

The system 100 can include a communication component 112, which can be alternatively or additionally referred to as a transaction manager herein. The communication component 112 can be used for transferring data and facilitating the exchange of information between the different system components of the system 100 or between the system 100 and one or more external elements. In some embodiments, the communication component 112 can include internal storage, for example, memory. In some embodiments, the communication component 112 can serve to queue information between components and user device(s), such that the system operates in an efficient manner without excessive lag times. The communication component 112 can communicate information from a user interface, the information including, for example, suggested treatment options and user feedback. The communication component 112 can communicate with a cloud computing environment. The communication component can, for example, obtain information from the cloud computing environment related to pooled statistics for many users over a given geographical area from the cloud computing environment and can communicate this information to the computing component 110, for example, for use in the determination of an optimal treatment.

The system 100 can include a user interface (not shown). In one or more example embodiments, the user interface can include a graphical user interface that can show an indication of the suggested treatment to the users and can collect the users decision and/or a rating and feedback by the user of such treatments. The user interface can also be used to obtain feedback from the user on the effectiveness of the current treatment. In some embodiments, the user interface may include a user application, browser executing on and/or accessible via the user device to interact with and/or cause display of information from the system and/or the user, as described herein.

The system 100 can be communicatively coupled, using the communication component 112, to a cloud computing environment (not shown). The cloud computing environment can offer one or more backend services. In some embodiments, the cloud computing environment can store information related to users (for example, user identity information, medical records, insurance information, data related to treatments, and the like), information related to the environment (environmental temperatures, humidity, weather, news events, and the like), overhead data (headers, data structures and files, and the like). In one or more example embodiments, the cloud computing environment that can pool data related to many users over a given geographical region (for example, the United States) to obtain data and/or determine statistics related to given treatments and/or pain perception models and systems. Such data and statistics can be used to provide enhanced treatment options to users.

Embodiments of devices described herein can employ artificial intelligence (AI) to facilitate automating one or more features described herein. The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform functions, actions, and/or determinations.

A classifier can map an input attribute vector, $z=(z1, z2, z3, z4, \ldots, zn)$, to a confidence that the input belongs to a class, as by $f(z)=\text{confidence(class)}$. Such classification can employ a probabilistic and/or statistical-based analysis (e.g., factoring into the analysis utilities and costs) to determinate an action to be automatically performed. A support vector machine (SVM) can be an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and/or probabilistic classification models providing different patterns of independence can be employed. Classification as used herein also is inclusive of statistical regression that is utilized to develop models of priority.

Figure 2:
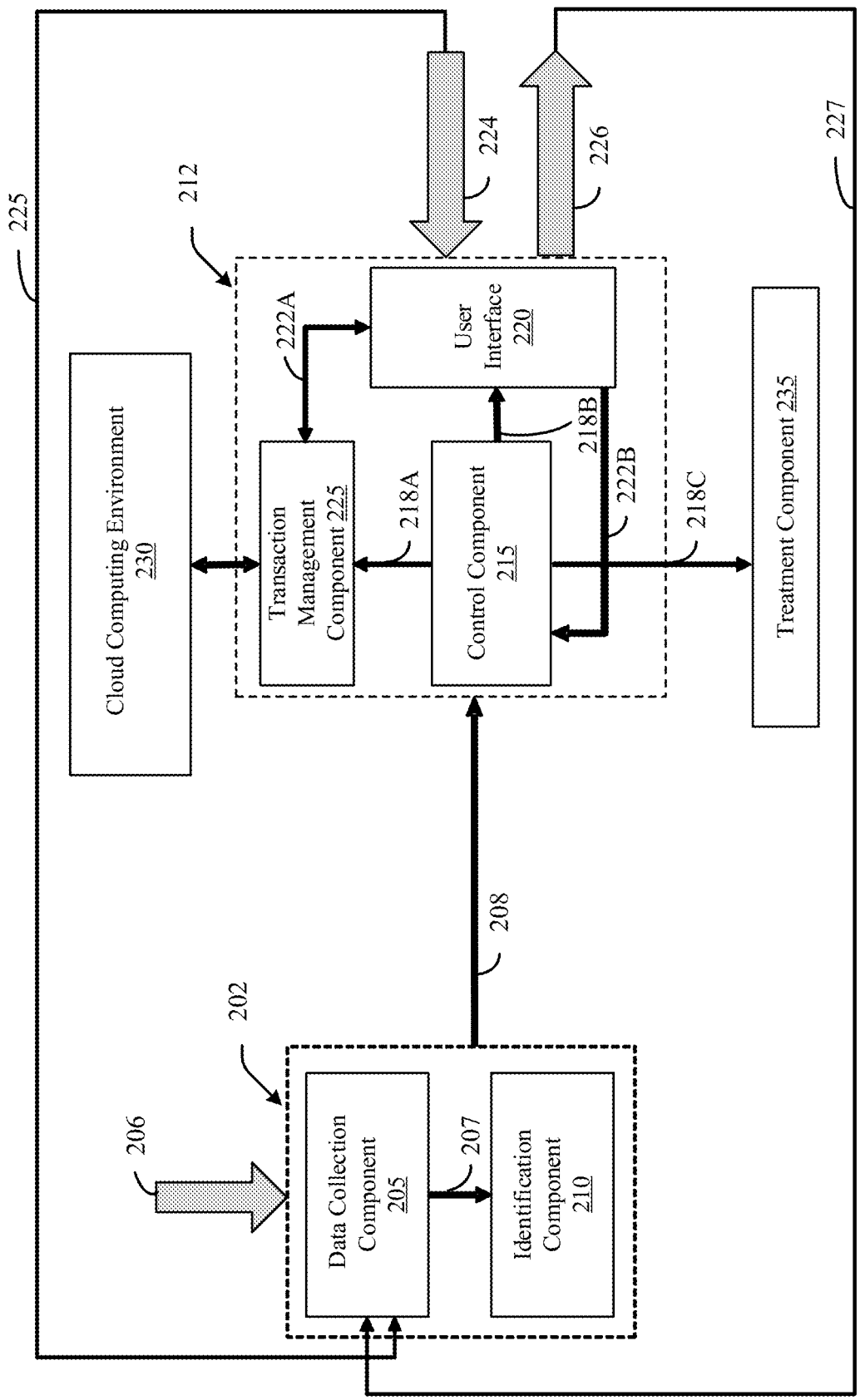
FIG. 2 illustrates a block diagram of an example, non-limiting system that can model pain perception in a human subject and recommend or apply treatments, in accordance with one or more embodiments described herein.

FIG. 2 illustrates a block diagram of an example, non-limiting system 200 that can that can model pain perception in a user and recommend or apply treatments, in accordance with one or more embodiments described herein. Embodiments of systems (e.g., system 200 and the like), apparatuses or processes in various embodiments of the present disclosure can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described. Repetitive description of like elements employed in one or more embodiments described herein is omitted for sake of brevity.

In one embodiment, the system 200 can include an online identification component 202. In one or more example embodiments, the online identification component 202 can include a data collection component 205 and an identification component 210, to be discussed. The online identification component 202 can serve to receive information from a local system 212 via a feedback loop 227. The information received from the local system 212 via the feedback loop 227 can include information related to a system and/or model determined by a control component 215 of the local system 212, a treatment determined by the control component 215, and/or user feedback obtained using the user interface 220. The information received from the local system 212 via the feedback loop 227 can be received at a data collection component 205, and can be used, for example, as inputs to an algorithm implemented at an identification component 210 of the online identification component 202 that can identify the dynamics of a system that models user's pain perception.

The online identification component 202 and various subcomponents and the local system 212 and various subcomponents may include or be in communication with one or more processing elements (also referred to as processors, processing circuitry, and/or similar terms used herein interchangeably) that communicate with other elements within the system 200 via a bus, for example. As will be understood, the processing element may be embodied in different ways. For example, the processing element may be embodied as one or more complex programmable logic devices (CPLDs), field programmable gate arrays (FPGAs), microprocessors, multi-core processors, coprocessing entities, application-specific instruction-set processors (ASIPs) or application-specific integrated circuits (ASICs), microcontrollers, microprocessors with accelerators to speed up training and inference, and/or controllers.

In one embodiment, the data collection component 205 can take as input 206 parameters including, but not limited to: (i) data regarding the user (including user preferences and psycho-physical variables like user's sleep, overall health condition, and the like) (ii) environmental conditions; (iii) past decisions; (iv) one or more treatments determined by the system 200. The data collection component 205 can manage the inputs 206 and can output 207 the managed inputs to the identification component 210 to facilitate online identification using an online identification component 202. In some embodiments, the online identification component 202 can send 208 the outputs to the control component 215.

In one or more example embodiments, the online identification component 202 of the system 200 can include an identification component 210. In one embodiment, the identification component 210 can receive 207 the output of the data collection component 205. The identification component 210 can further implement one or more algorithms that can identify the dynamics of a system corresponding to the inputs 206. For example, the identification component 210 can determine whether the system is linear or nonlinear, and can determine the system's mathematical order (e.g., order of non-linearity). In some embodiments, the identification component 210 can determine a model based on the input 206 comprising parameters and uncertainties associated with the parameters. In one embodiment, uncertainties can include a sensor uncertainty or a user-provided uncertainty. In an embodiment, a sensor uncertainty can include, for example, an uncertainty in the measurement of an environmental variable such as temperature, or a user facial expression. A user-provided uncertainty can involve a user being presented a query relating to the effectiveness of a treatment. The user may be asked to provide a numerical score to a pain felt before and after the application of the treatment. The user may be further asked to include a numerical uncertainty associated with the numerical score. For example, the user may indicate that the pain is 7 out of 10 on a scale of 1 to 10, where 1 represents the least pain and 10 represents the most pain. The user may further designate that he/she has a 1-point uncertainty in their evaluation. In other words, that the pain may have an intensity of 6 out of 10, or 8 out of 10 in the above described case. The uncertainty may reflect a time-based uncertainty of the pain felt by the user. That is, the user may feel more pain at a given time in a predetermined time-interval or less pain at a given time in the time interval. In some embodiments, the identification component 210 can determine the system online, that is, there may be no further need to include checkpoints or run specific experiments to identify the system. In one or more example embodiments, the system can be online, that is connected to one or more networks, such as a local intranet or the Internet. In some embodiments, the model and/or the system can be continuously updated based on one or more machine learning processes.

In one embodiment, the system 200 can include a local system 212. The local system 212 can include components that are at least partially implemented locally on a device, for example, a user device. In some embodiments, the user device can include one or more computers, computing entities, desktop computers, mobile phones, tablets, phablets, notebooks, laptops, distributed systems, gaming consoles (e.g., Xbox, Play Station, Wii), watches, glasses, iBeacons, proximity beacons, key fobs, radio frequency identification (RFID) tags, ear pieces, televisions, dongles, cameras, wristbands, wearable items/devices, kiosks, input terminals, servers or server networks, blades, gateways, switches, processing devices, processing entities, set-top boxes, relays, routers, network access points, base stations, the like, and/or any combination of such devices or entities. The user device can include an antenna, a transmitter (e.g., radio), a receiver (e.g., radio), and a processing element (e.g., CPLDs, field programmable gate arrays (FPGAs), microprocessors, multi-core processors, coprocessing entities, ASIPs, or application-specific integrated circuits (ASICs), microcontrollers, microprocessors with accelerators to speed up training and inference, and/or controllers) that provides signals to and receives signals from the transmitter and receiver, respectively. Further the user device may include or be in communication with one or more input elements, such as a keyboard input, a mouse input, a touch screen/display input, motion input, movement input, audio input, pointing device input, joystick input, keypad input, and/or the like. The user device may also include or be in communication with one or more output elements (not shown), such as audio output, video output, screen/display output, motion output, movement output, and/or the like.

In some embodiments, the local system 212 can include a control component 215, a transaction manager 225, and a user interface 220, to be discussed below. In some embodiments, the local system can communicate with a cloud computing environment 230, to be discussed below. In one or more example embodiments, the local system can communicate with the cloud computing environment 230 using a transaction manager 225. In some embodiments, the local system can receive information from the online identification component 202 using a connection 208. The information can include information generated by the online identification component 202 (for example, at the identification component 210) related to the dynamics of a system that models user's pain perception.

In one or more example embodiments, the local system 212 can receive 224 information from a feedforward loop 223 connected to the online identification component 202. For example, the local system 212 can receive 224 information related to one or more inputs 206 that were discussed above in addition to the dynamics of a system that models user's pain perception as determined, for example, by the identification component 210. In one or more example embodiments, the local system 212 can communicate signals to the treatment component 235. The local system 212 can communicate such signals, for example, by means of the control component 215.

In one embodiment, the system 200 can include a control component 215. The control component 215 can compute, in real time, an optimal treatment for the user, based on the user's current state and based on the model that has been identified. In some embodiments, the control component 215 can exchange information to other components in the system 200 by communicating 218a through the transaction manager 225. In one or more example embodiments, the control component 216 can be configured to update and adapt the treatment, in real time, as a function of the parameters gathered and stored in the data collection component 205. Moreover, the control component 215 can be configured to operate in a recommender mode, where a recommendation for a treatment can be sent 218b to the user, for example, at a user interface displayed on a user device (e.g., mobile device, laptop, and the like). In one or more example embodiments, the control component 215 can be configured to operate in a control mode where signals corresponding to a given treatment can be automatically generated and sent 218c to a treatment component 235. For example, electromagnetic signals can be generated by the control component 216 and sent to the treatment component 235, which can, for example, include an electronic device that applies heat or electromagnetic radiation to a portion of the user's body for reducing pain.

In one embodiment, the system 200 can include a user interface 220. The user interface 220 can receive 218b the output of the control component 215 as input. In one or more example embodiments, if the system 200 is in a recommender mode of operation, the user interface 220 can show recommendations for treatments to the user. In one or more example embodiments, the user interface 220 can include a graphical user interface (GUI) that can show an indication of the suggested treatment to the users and can collect the user's decision and/or a rating and feedback by the user of such treatments. Such decisions can be provided 222a to the transactions manager 225 and can also be fed back 222b to the control component 215. The user interface 220 can also be used to have a feedback from the user on the effectiveness of the current treatment.

In some embodiments, the user interface may include a user application, browser executing on and/or accessible via the user device to interact with and/or cause display of information from the system 200 and/or the user, as described herein. The user interface 220 can comprise any suitable devices or interfaces allowing the user device to receive data, such as a keypad (hard or soft), a touch display, voice/speech or motion interfaces, or other input device. In embodiments including a keypad, the keypad can include (or cause display of) the typical numeric (0-9) and related keys (#, *), and other keys used for operating the user device and may include a full set of alphabetic keys or set of keys that may be activated to provide a full set of alphanumeric keys.

In one embodiment, the system 200 can include a transaction manager 225. The transaction manager 225 can facilitate the exchange of information between the different components shown in system 200. In some embodiments, the transaction manager 225 can include storage, for example, memory. In some embodiments, the transaction manager 225 can serve to queue information between components and user device(s), such that the system operates in an efficient manner without excessive lag times. In some embodiments, the transaction manager 225 can receive 218a information from the control component 215. The information received 218a from the control component 215 can be used to schedule communications between components in the system 200. The transaction manager 225 can communicate 222a information from a user interface 220, the information including, for example, suggested treatment options and user feedback. The transaction manager 225 can communicate with the cloud computing environment 230. The transaction manager 225 can, for example, obtain information related to pooled statistics for many users over a given geographical area from the cloud computing environment 230 and can communicate this information to the control component 215, for example, for use in the determination of an optimal treatment.

In some embodiments, such communications mediated by the transaction manager 225 or other various components in the system 200 may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the transaction manager 225 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, ZigBee, Bluetooth protocols, wireless universal serial bus (USB) protocols, and/or any other wireless protocol.

In one or more example embodiments, the system 200 can include a cloud computing environment 230. The cloud computing environment 230 can offer one or more backend services. In some embodiments, the cloud computing environment 230 can store information related to users (for example, user identity information, medical records, insurance information, data related to treatments, and the like), information related to the environment (environmental temperatures, humidity, weather, news events, and the like), overhead data (headers, data structures and files, and the like). The cloud computing environment 230 can further run algorithms or sub-algorithms that can substitute or supplement the local system 212 or the online identification component 202 in the determination of systems, models, and/or treatments associated with a user. In one or more example embodiments, the cloud computing environment 230 can pool data related to many users over a given geographical region (for example, the United States) to obtain data and/or determine statistics related to given treatments and/or pain perception models and systems. Such data and statistics can be used to provide enhanced treatment options to users. In some embodiments, the cloud computing environment 230 can be similar, but not necessarily identical to, the cloud computing environment that was shown and described in connection with FIG. 1. For example, cloud computing environment can include one or more cloud computing nodes with which local computing devices used by cloud consumers, such as, for example, personal digital assistant (PDA) or cellular telephone, desktop computer, laptop computer, and/or automobile computer system may communicate. Nodes may communicate with one another. They may be grouped physically or virtually, in one or more networks, such as Private, Community, Public, or Hybrid clouds, or a combination thereof. This allows cloud computing environment to offer infrastructure, platforms and/or software as services for which a cloud consumer does not need to maintain resources on a local computing device.

Figure 3:
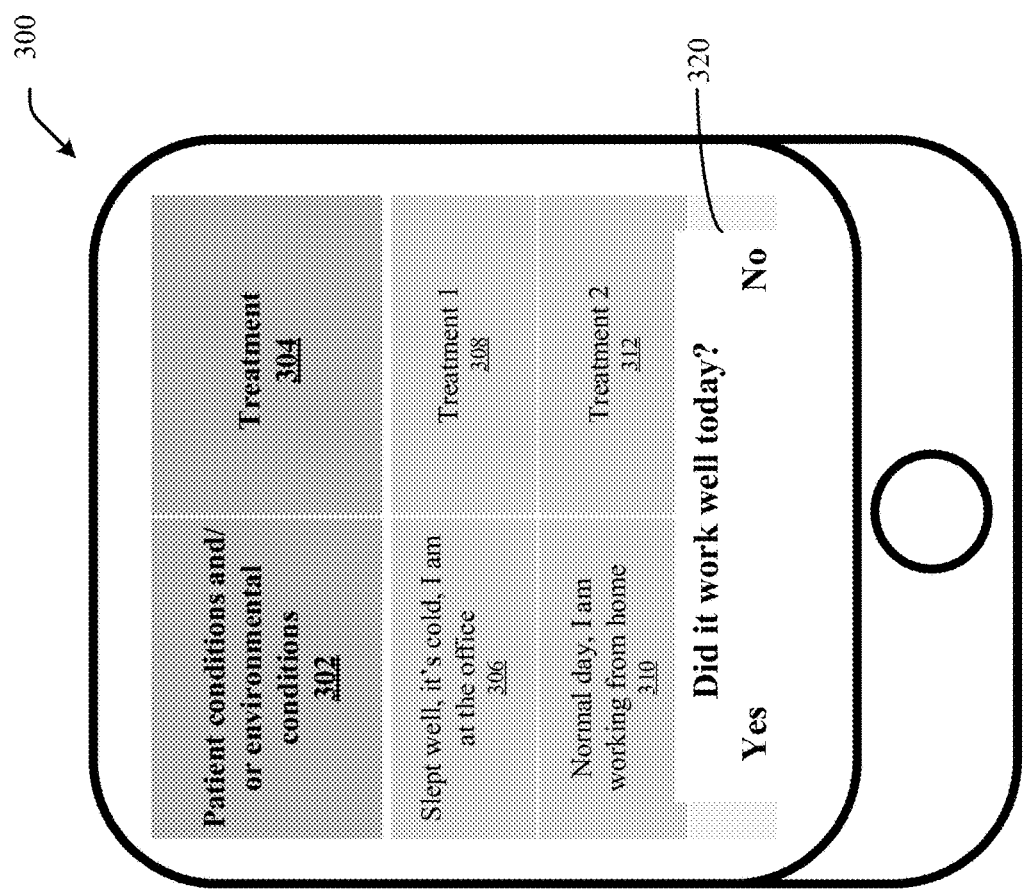
FIG. 3 illustrates a block diagram of an example, non-limiting system that can gather user feedback, in accordance with one or more embodiments described herein.

FIG. 3 illustrates a block diagram of an example, non-limiting system that can gather user feedback, in accordance with one or more embodiments described herein. Repetitive description of like elements employed in one or more embodiments described herein is omitted for sake of brevity. In one or more example embodiments, the system can include a user device that can include user interface 300. The user interface 300 can show an indication of the suggested treatment to the users and can collect the users decision and/or a rating and feedback by the user of such treatments. The user interface 300 can also be used to obtain feedback from the user on the effectiveness of the current treatment. In some embodiments, the user interface 300 may include a user application, browser executing on and/or accessible via the user device to interact with and/or cause display of information from the system and/or the user, as described herein.

The user interface 300 can include a table 301. The table 301 can include patient conditions and/or environmental conditions 302. For example, the patient conditions and/or environmental conditions 302 can include descriptions provided by the user. For example, the patient conditions and/or environmental conditions 302 can include such descriptions as "Slept well, it's cold, I am at the office" 306, and another description "Normal day, I am working from home" 310. The table 301 can further include treatments 304, e.g., proposed treatments, for example, treatment 1 308 that can correspond to description 306, or treatment 2 312 that can correspond to description 310. For example, treatment 1 308 can include a normal-intensity pulsed electromagnetic radiation treatment applied by a medical device. Treatment 2 312 can include a yoga and stretching regimen. The treatments 304 such as treatment 1 308 and/or treatment 2 312 can include hyperlinks that the user can select for further information. The user interface 300 can include a feedback interface 320 that can ask the user a question, for example, "Did it work well today?" and offer the user the option of selecting "yes" or "no." Alternatively or additionally, the feedback interface 320 can include an interface which allows the user to score the treatment instead of merely providing a yes/no answer to a question. The feedback interface 320 can include a series of questions, for example, questions related to the effectiveness of the treatment, the general physical or psychological condition of the patient, and the like. The feedback interface 320 can take user feedback and transmit to one or more internal components, for example, a control component (like control component 215 shown and described in connection with FIG. 2), to compute a dynamical system or a model or an updated dynamical system or model.

The system can include a data analysis component (not shown) that can use natural language processing to extract the one or more features, wherein the one or more features can be n-grams (e.g., unigrams and/or bigrams), modal verbs, action verbs, and the like from one or more sentences of the descriptions (such as descriptions 306 and/or 308) regarding user (e.g., via interaction with one or more chatbots and/or via communication with another individual, such as a caretaker). Subsequently, the data analysis component can train a classifier program (e.g., such as a support vector machine) based on the one or more extracted features to determine a condition and/or treatment associated with the user.

In some embodiments, the user interface 300 may include a user application, browser executing on and/or accessible via the user device to interact with and/or cause display of information from the system and/or the user, as described herein. The user interface 300 can comprise any suitable devices or interfaces allowing the user device to receive data, such as a keypad (hard or soft), a touch display, voice/speech or motion interfaces, or other input device. In embodiments including a keypad, the keypad can include (or cause display of) the typical numeric (0-9) and related keys (#, *), and other keys used for operating the user device and may include a full set of alphabetic keys or set of keys that may be activated to provide a full set of alphanumeric keys.

Figure 4A:
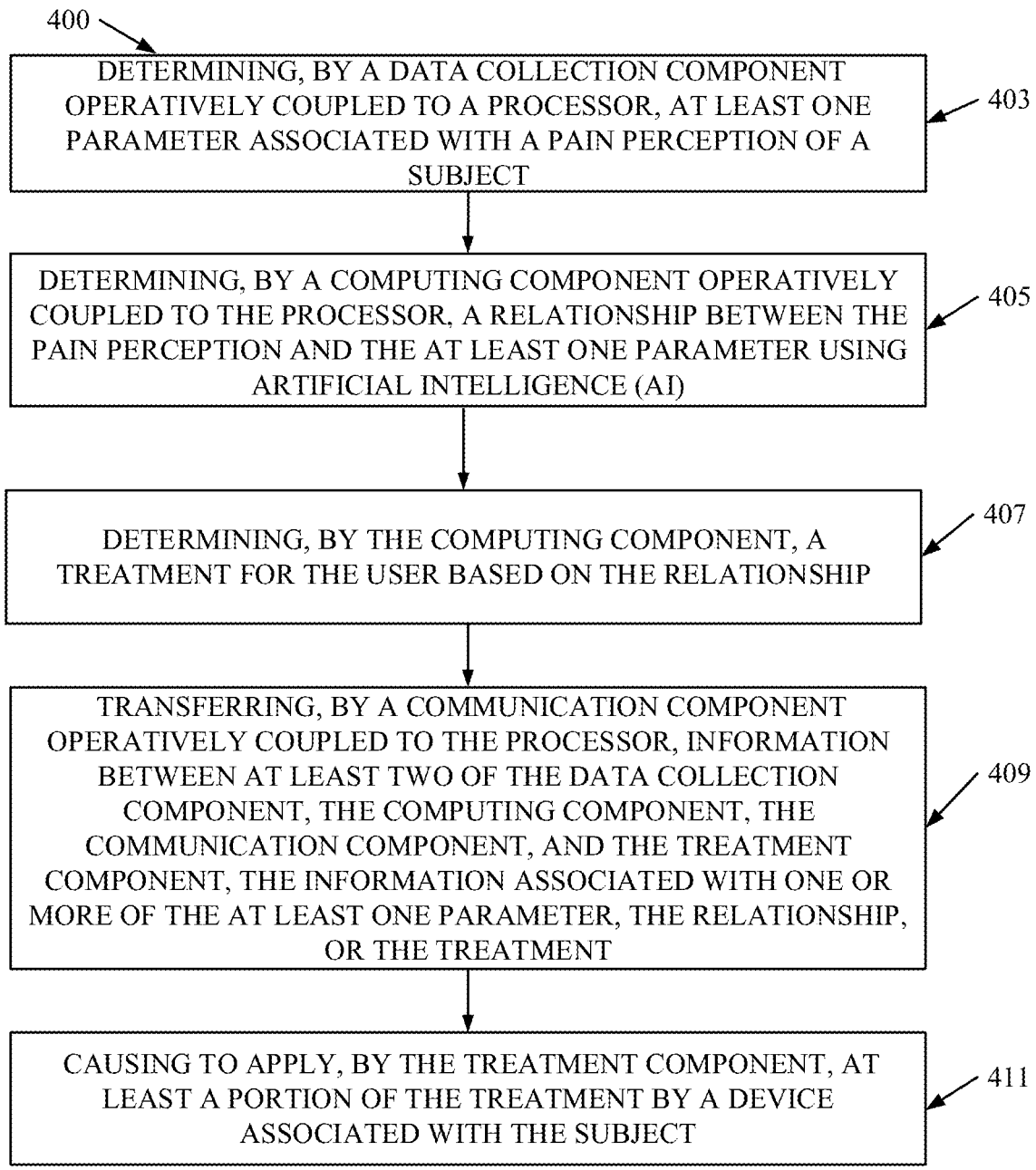
FIGS. 4A, 4B, 4C, and 4D illustrate flow diagrams of example, non-limiting methods that can facilitate pain management for human subjects, in accordance with one or more embodiments described herein.

FIG. 4A shows a diagram of a flow chart 400 that shows embodiments of example operations of the system, in accordance with example embodiments of the disclosure. Repetitive description of like elements employed in one or more embodiments described herein is omitted for sake of brevity. At block 403, a data collection component can determine at least one parameter associated with a pain perception of a user. In some aspects, the data collection component can include one or more sensors to gather relevant information, such as a user temperature, an environmental temperature, one or more facial features of the user, a gait or limp associated with the user's movements, sounds (e.g., groans, screams, and the like) from the user, and the like. The sensors can include infrared sensors, microphones, cameras and associated facial-recognition systems, and the like.

The data collection component can associate a measurement uncertainty with any of the variables measured by the sensors. Non-limiting examples can include an uncertainty in the temperature measurement of a user or a user environment, an uncertainty in the severity of a sound emanated by the user or an association of the sound with a pain, and the like. In other examples, the uncertainty can be based on user feedback at a user device. For example, a user device can ask a question about the user's level of uncertainty in the amount of pain being experienced by the user.

At block 405, a computing component can determine a relationship between the pain perception and the at least one parameter using artificial intelligence (AI). In some embodiments, the computing component can generate a model that can capture embodiments of pain perception of users and the relationship of such pain perception with one or more treatments. In some embodiments, the computing component can generate a non-linear dynamical system or model of an arbitrary mathematical order that can relate the treatment to a quantity of interest, for example, a measure of the pain or a variable that correlates with pain (for example, a quality of sleep, a quality of life, an overall satisfaction, and the like associated with user). In some embodiments, based on the dynamic system or model, the computing component can implement a real-time, closed-loop adaptive model that is able to determine an optimized treatment for the user. In one or more example embodiments, as the dynamic system or model changes over time, the data collection unit can remeasure the quantity of interest, and the computing component can reanalyze the model's parameters. In one embodiment, the model parameters can be taken as input by the computing component which can adapt in real-time based on the time-evolution of the model's parameters.

As mentioned, the computing component can use artificial intelligence (AI) to facilitate automating one or more features described herein. The components can employ various AI-based schemes for carrying out various embodiments/examples disclosed herein. To provide for or aid in the numerous determinations (e.g., determine, ascertain, infer, calculate, predict, prognose, estimate, derive, forecast, detect, compute) described herein, components described herein can examine the entirety or a subset of the data to which it is granted access and can provide for reasoning about or determine states of the system, environment, etc. from a set of observations as captured via events and/or data. Determinations can be employed to identify a specific context or action, or can generate a probability distribution over states, for example. The determinations can be probabilistic—that is, the computation of a probability distribution over states of interest based on a consideration of data and events. Determinations can also refer to techniques employed for composing higher-level events from a set of events and/or data.

Such determinations can result in the construction of new events or actions from a set of observed events and/or stored event data, whether the events are correlated in close temporal proximity, and whether the events and data come from one or several event and data sources. Components disclosed herein can employ various classification (explicitly trained (e.g., via training data) as well as implicitly trained (e.g., via observing behavior, preferences, historical information, receiving extrinsic information, etc.)) schemes and/ or systems (e.g., support vector machines, neural networks, expert systems, Bayesian belief networks, fuzzy logic, data fusion engines, etc.) in connection with performing automatic and/or determined action in connection with the claimed subject matter. Thus, classification schemes and/or systems can be used to automatically learn and perform a number of functions, actions, and/or determinations.

At block 407, the computing component can determine a treatment for the user based on the relationship. In one or more example embodiments, the computing component can determine, based on the dynamic model, what an optimal treatment for the user entails, specific for the user's conditions. In one or more example embodiments, the computing component may not be restricted to choose between a set of pre-determined treatments but can implement machine learning based on a user's past behavior and can generate new treatments accordingly.

At bock 409, a communication component can transfer information between at least two of the data collection component, the computing component, the communication component, and the treatment component, the information associated with one or more of the at least one parameter, the relationship, or the treatment. The communication component can be used for transferring data and facilitating the exchange of information between the different system components or between the components and one or more external elements. In some embodiments, the communication component can include internal storage, for example, memory. In some embodiments, the communication component can serve to queue information between components and user device(s), such that the system operates in an efficient manner without excessive lag times. The communication component can communicate information from a user interface, the information including, for example, suggested treatment options and user feedback. The communication component can communicate with a cloud computing environment. The communication component can, for example, obtain information from the cloud computing environment related to pooled statistics for many users over a given geographical area from the cloud computing environment and can communicate this information to the computing component, for example, for use in the determination of an optimal treatment.

At block 411, a treatment component can apply at least a portion of the treatment by a device associated with the user. In one or more example embodiments, the treatment component can deliver or configure another device to deliver the treatment to the user based on the treatment. For example, the treatment component can send information describing electrical stimuli (e.g., magnitude, frequency, waveform type, and the like) to be applied one or more electrodes attached to the user's body. In some aspects, the electrical stimuli can be applied using a non-implantable device.

In another example, a medication can be released through a patch or an implantable device based on instructions provided by the treatment component for pain management. The treatment component can also facilitate the generation of one or more prescriptions, and make recommendations to a medical practitioner, such as a doctor.

Figure 4B:
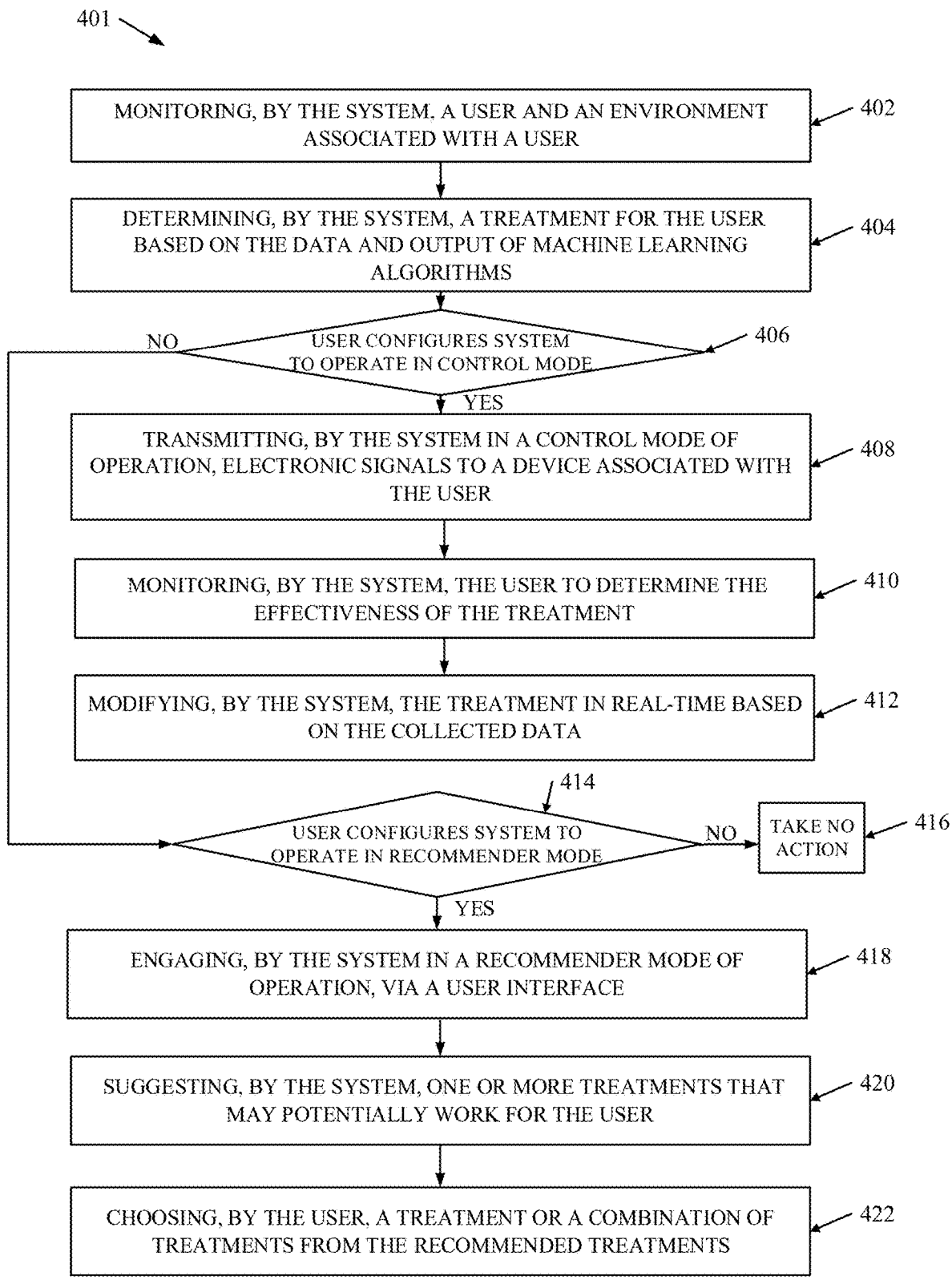

FIG. 4B shows a diagram of a flow chart 401 that shows embodiments of example operations of the system, in accordance with example embodiments of the disclosure. Repetitive description of like elements employed in one or more embodiments described herein is omitted for sake of brevity. At block 402, the system can monitor a user and an environment associated with a user. In some embodiments, the system can run seamlessly; for example, the system may not require adjustment or partial input or updating from the user. The system can run in a silent-mode of operation. The system can record data related to the activities of the user and one or more environmental conditions. In some embodiments, the system can use the data gathered as input to one or more machine learning algorithms. In some embodiments, the system can monitor the user by using one or more sensors. The sensors can be part of a user device, for example, a smart-watch, a mobile phone, a home-camera, a webcam, and the like. For example, the system can monitor a heart-rate of the user using a heart-rate monitor. For example, an increase in the heart rate of the user can correlate with increased pain. In one or more example embodiments, the system can monitor facial expressions of the user, for example, using a camera to capture grimaces which can be correlated with pain, for facial recognition and image analysis by one or more facial recognition algorithms being run by the system. In one embodiment, the system can use an infrared sensor to monitor the temperate of a portion of a user's body. For example, an increase in blood flow to a region of the body having pain may correlate with increased pain at that region.

In one or more example embodiments, the system can monitor a gait or walking pattern of the user, for example, using a camera to capture images or videos of a limp which can be correlated with pain; the system can implement one or more computer vision and/or image analysis methods to extract one or more features or conditions from the captured images or videos. In one embodiment, the system can use a humidity or chemical sensor to monitor the odors or sweat emanating from a portion of a user's body. For example, an increase in certain volatile organic compounds (VOCs) and/or sweat emanating from a region in the user's body may correlate with increased pain at that region. In one or more example embodiments, the system can monitor a sound of the user, for example, using a microphone to capture audio of a user. For example, moans, groans, and/or screams from the user can be captured by the sensor and can correlate with an occurrence and intensity of pain for the user. Further the system can implement one or more audio analysis methods to extract one or more features or conditions from the captured sounds.

At block 404, the system can determine a given treatment for the given user based on the data and output of the machine learning algorithms. In one or more example embodiments, the treatment can be updated based on changes in the data and output of the algorithms. In some embodiments, the treatment can include any suitable treatment, excluding treatments having implantable devices for electronic stimulation of a user's body for pain management. In one or more example embodiments, the treatment can include one or more alternative therapies, such as stretches, yoga, and the like. Such therapies may be preferred by the user (as indicated by a user preference submitted by the user) or may be preferred by the system to reduce the incidence of overdependence on medication, for example, opioid medication.

At block 406, the user can configure the system to operate in a control mode of operation. If the user does not configure the system to operate in the control mode of operation, the flow can continue at block 414. If the user does configure the system to operate in a control mode of operation, then at block 408, electronic signals can be transmitted by the system to a non-implantable device associated with the user. In some embodiments, the electronic signals can correlate with stimuli to be applied by a pain management device to reduce pain at a painful region of the user's body. The electronic signals can include electromagnetic pulses that deliver heat and/or radiation (including laser radiation) to the painful region of the user's body. The electronic signals can indicate a frequency, magnitude, and/or phase of an electromagnetic radiation to be applied to the user's body. The control mode of operation can be configured by the user. In some embodiments, the system may present the option of operating in a control mode of operation to the user at a user interface.

At block 410, the system can monitor the user to determine the effectiveness of the treatment. For example, the system can monitor a heart-rate of the user using a heart-rate monitor. For example, an increase in the heart rate of the user can correlate with increased pain, while a reduced heart rate may correlate with a reduction in pain and therefore a higher treatment effectiveness. In one or more example embodiments, the system can monitor facial expressions of the user as described above, and a reduction in the frequency or intensity of certain facial expression such as grimaces can correlate with a reduction in pain and a higher treatment effectiveness. In one embodiment, the system can use an infrared sensor to monitor the temperate of a portion of a user's body. For example, a decrease in blood flow to a region of the body having pain may correlate with decreased pain at that region and a higher treatment effectiveness. In one or more example embodiments, the system can monitor a gait or walking pattern of the user, for example, using a camera to capture images or videos of a limp which can be correlated with pain as described above. A reduction in certain features associated with the walking pattern of the user, for example, a reduction in the limp of the user as determined by image processing algorithms can collate with a reduction in pain and a higher treatment effectiveness. In one embodiment, the system can use a humidity or chemical sensor to monitor the odors or sweat emanating from a portion of a user's body. For example, a decrease in certain volatile organic compounds and/or sweat emanating from a region in the user's body may correlate with reduced pain at that region and higher treatment effective. In one or more example embodiments, the system can monitor sounds of the user, for example, using a microphone to capture audio of a user. For example, a reduction in the frequency or intensity of moans, groans, and/or screams from the user can be captured by the sensor and can correlate with a reduction of the and intensity of pain for the user.

At block 412, the treatment can be modified in real-time, based on the data collected in previous steps. For example, the treatment can be adapted based on a feedback loop, similar to the feedback loop 227 shown and described in connection with FIG. 2. In some embodiments, modified electronic signals can be generated and can correlate with stimuli to be applied by a non-implantable pain management device to reduce pain at a painful region of the user's body. As mentioned, the electronic signals can include electromagnetic pulses that deliver heat and/or radiation (including laser radiation) to the painful region of the user's body. The electronic signals can indicate an updated frequency, an updated magnitude, and/or an updated phase of an electromagnetic radiation to be applied to the user's body. For example, if the data collected in the previous steps indicates that the pain is increasing for the user, then the electronic signal can indicate an increased frequency and/or an increased magnitude for electromagnetic radiation being applied at the region of pain on the user's body.

At block 414, the user can configure the system to operate in a recommender mode of operation. If the user does not configure the system to operate in the recommender mode of operation, the flow can continue at block 416, where the system can take no further action.

If the user configures the system to operate in a recommender mode of operation, then at block 418, the user can be engaged via a user interface. For example, the user can be engaged for feedback when treatments are determined. For example, the user can provide a ranking of possible treatment options based on the user's preference. For example, some users may prefer to apply electromagnetic radiation via a non-implantable device to the site of the pain rather than taking a prescription medication for pain management. In some embodiments, the user can be engaged using an audio-visual application on a user device, for example, a smartphone app or a laptop application or a website-run application. The audio-visual application can present queries in text, audio, or video format and can receive user responses via text, audio, or video format. Accordingly, the audio-visual application can include a speech-conversion engine implemented to receive speech from a user and convert that into text for analysis by algorithms and techniques run by the system as described herein.

At block 420, the system can suggest one or more treatments that may potentially work best for the user. In some embodiments, the one or more treatments can be based on the user's psycho-physical condition data and the environmental condition data collected by the system in the preceding steps. In one or more example embodiments, the system may be not constrained to pick a treatment among a set of pre-defined treatments and can propose new treatments, as described variously herein.

At block 422, the user can choose a treatment or a combination of treatments from the treatments recommended. The user can for example, choose a treatment that includes obtaining a prescription medication from an authorized medical professional or taking a prescription medication at a predetermined dosage and predetermined time as recommended by the system.

Examples of medications that can be recommended in the treatments can include analgesics are nonsteroidal anti-inflammatory medications (NSAIDs). In some embodiments, acetaminophen may be administered as a single medication or in combination with other analgesics (both NSAIDs and opioids). Further examples of medications that can be recommended in the treatments includes weak opioids such as tramadol, or a combination of an opioid with acetaminophen can be used such as Percocet, Vicodin, or Norco. In some embodiments, morphine and semi-synthetic derivatives of morphine such as hydromorphone (Dilaudid), oxymorphone (Numorphan, Opana), nicomorphine (Vilan), and/or hydromorphinol can be recommended. In one or more example embodiments, Fentanyl can be recommended. Oxycodone can be recommended for the relief of serious chronic pain. Diamorphine and buprenorphine can also be recommended. Other medications such as piritramide and ketobemidone can be recommended for severe pain. For moderate pain, tramadol, codeine, dihydrocodeine, hydrocodone, nicocodeine, ethylmorphine and propoxyphene and dextropropoxyphene can be recommended.

Figure 4C:
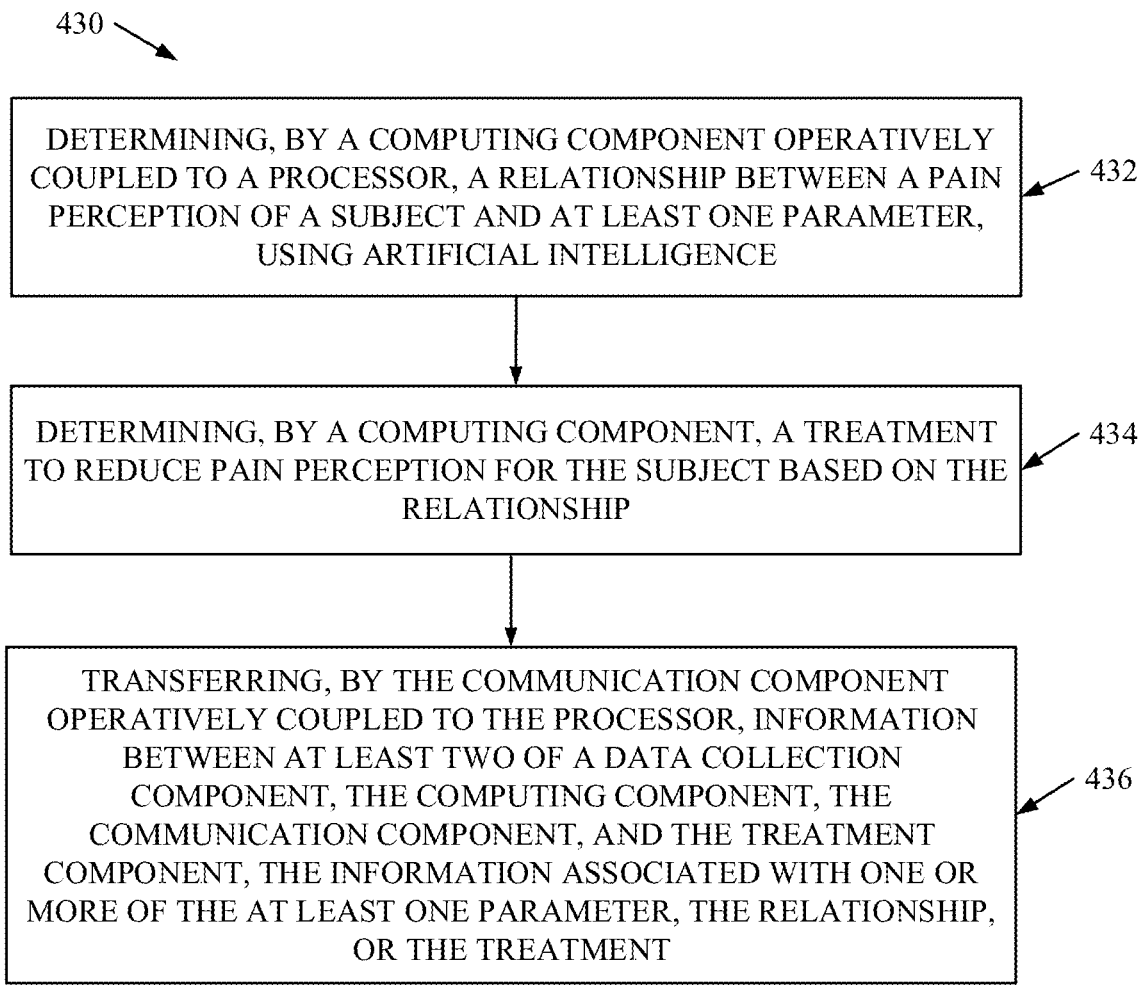

FIG. 4C shows a diagram of a flow chart 430 that shows embodiments of an example method, in accordance with example embodiments of the disclosure. At block 432, a computing component operatively coupled to a processor, can determine a relationship between a pain perception of a subject and at least one parameter, using artificial intelligence. At block 434, the computing component can determine a treatment to reduce pain perception for the subject based on the relationship. At block 436, the communication component operatively coupled to the processor can transfer information between at least two of a data collection component, the computing component, the communication component, and the treatment component, the information being associated with one or more of the at least one parameter, the relationship, or the treatment.

Figure 4D:
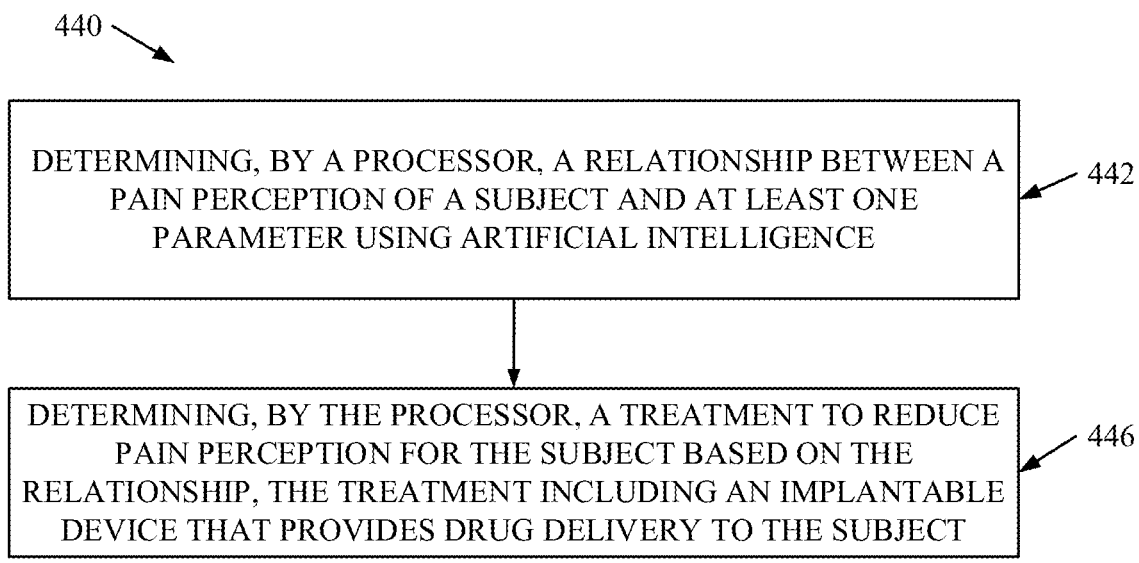

FIG. 4D shows a diagram of a flow chart 440 that shows embodiments of example operations of a computer program product, in accordance with example embodiments of the disclosure. At block 442, a relationship can be determined, by a processor, between a pain perception of a subject and at least one parameter using artificial intelligence. At block 444, a treatment can be determined, by the processor, to reduce pain perception for the subject based on the relationship, the treatment including an implantable device that provides medication delivery to the subject.

Embodiments of the subject matter and the operations described herein can be implemented in digital electronic circuitry, or in computer software, firmware, or hardware, including the structures disclosed in this specification and their structural equivalents, or in combinations of one or more of them. Embodiments of the subject matter described herein can be implemented as one or more computer programs, i.e., one or more components of computer program instructions, encoded on computer storage medium for execution by, or to control the operation of, information/data processing apparatus. Alternatively, or in addition, the program instructions can be encoded on an artificially generated propagated signal, e.g., a machine-generated electrical, optical, or electromagnetic signal, which is generated to encode information/data for transmission to suitable receiver apparatus for execution by an information/data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described herein can be implemented as operations performed by an information/data processing apparatus on information/data stored on one or more computer-readable storage devices or received from other sources.

Figure 5:
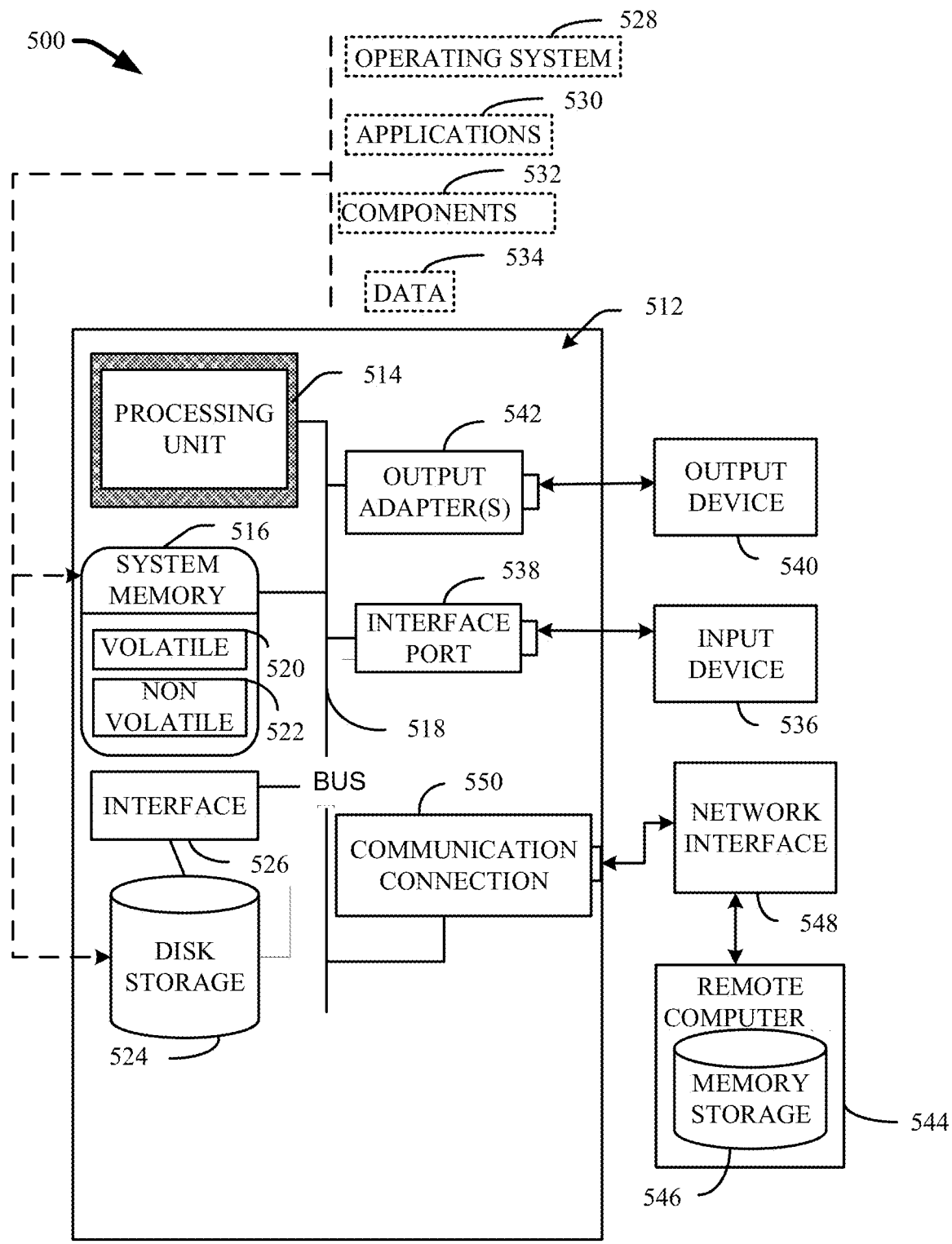
FIG. 5 illustrates a block diagram of an example, non-limiting operating environment in which one or more embodiments described herein can be facilitated.

To provide a context for the various embodiments of the disclosed subject matter, FIG. 5 as well as the following discussion are intended to provide a general description of a suitable environment in which the various embodiments of the disclosed subject matter can be implemented. FIG. 5 illustrates a block diagram of an example, non-limiting operating environment in which one or more embodiments described herein can be facilitated. Repetitive description of like elements employed in other embodiments described herein is omitted for sake of brevity. With reference to FIG. 5, a suitable operating environment 500 for implementing various embodiments of this disclosure can include a computer 512. The computer 512 can also include a processing component 514, a system memory 516, and a system bus 518. The system bus 518 can operably couple system components including, but not limited to, the system memory 516 to the processing component 514. The processing component 514 can be any of various available processors. Dual microprocessors and other multiprocessor architectures also can be employed as the processing component 514. The system bus 518 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 516 can also include volatile memory 520 and nonvolatile memory 522. The basic input/output system (BIOS), containing the basic routines to transfer information between elements within the computer 512, such as during start-up, can be stored in nonvolatile memory 522. By way of illustration, and not limitation, nonvolatile memory 522 can include read only memory (ROM), programmable ROM (PROM), electrically programmable ROM (EPROM), electrically erasable programmable ROM (EEPROM), flash memory, or nonvolatile random-access memory (RAM) (e.g., ferroelectric RAM (FeRAM). Volatile memory 520 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 512 can also include removable/non-removable, volatile/non-volatile computer storage media. FIG. 5 illustrates, for example, a disk storage 524. Disk storage 524 can also include, but is not limited to, devices like a magnetic disk drive, floppy disk drive, tape drive, Jaz drive, Zip drive, LS-100 drive, flash memory card, or memory stick. The disk storage 524 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 524 to the system bus 518, a removable or non-removable interface can be used, such as interface 526. FIG. 5 also depicts software that can act as an intermediary between users and the basic computer resources described in the suitable operating environment 500. Such software can also include, for example, an operating system 528. Operating system 528, which can be stored on disk storage 524, acts to control and allocate resources of the computer 512. System applications 530 can take advantage of the management of resources by operating system 528 through program components 532 and program data 534, e.g., stored either in system memory 516 or on disk storage 524. It is to be appreciated that this disclosure can be implemented with various operating systems or combinations of operating systems. A user enters commands or information into the computer 512 through one or more input devices 536. Input devices 535 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing component 514 through the system bus 518 via one or more interface ports 538. The one or more Interface ports 538 can include, for example, a serial port, a parallel port, a game port, and a universal serial bus (USB). One or more output devices 540 can use some of the same type of ports as input device 536. Thus, for example, a USB port can be used to provide input to computer 512, and to output information from computer 512 to an output device 540. Output adapter 542 can be provided to illustrate that there are some output devices 540 like monitors, speakers, and printers, among other output devices 540, which require special adapters. The output adapters 542 can include, by way of illustration and not limitation, video and sound cards that provide a means of connection between the output device 540 and the system bus 518. It should be noted that other devices and/or systems of devices provide both input and output capabilities such as one or more remote computers 544.

Computer 512 can operate in a networked environment using logical connections to one or more remote computers, such as remote computer 544. The remote computer 544 can be a computer, a server, a router, a network PC, a workstation, a microprocessor based appliance, a peer device or other common network node and the like, and typically can also include many or all elements described relative to computer 512. For purposes of brevity, only a memory storage device 546 is illustrated with remote computer 544. Remote computer 544 can be logically connected to computer 512 through a network interface 548 and then physically connected via communication connection 550. Further, operation can be distributed across multiple (local and remote) systems. Network interface 548 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 550 refers to the hardware/software employed to connect the network interface 548 to the system bus 518. While communication connection 550 is shown for illustrative clarity inside computer 512, it can also be external to computer 512. The hardware/software for connection to the network interface 548 can also include, for exemplary purposes only, internal and external technologies such as, modems including regular telephone grade modems, cable modems and DSL modems, ISDN adapters, and Ethernet cards.

As mentioned herein, the systems, methods, and apparatuses described can be used in connection with cloud computing environments. Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows: Private cloud: the cloud infrastructure is operated solely for an organization. It may be managed by the organization or a third party and may exist on-premises or off-premises. Community cloud: the cloud infrastructure is shared by several organizations and supports a specific Community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds). A cloud computing environment is service oriented with a focus on statelessness, low coupling, modularity, and semantic interoperability. At the heart of cloud computing is an infrastructure that includes a network of interconnected nodes.

Figure 6:
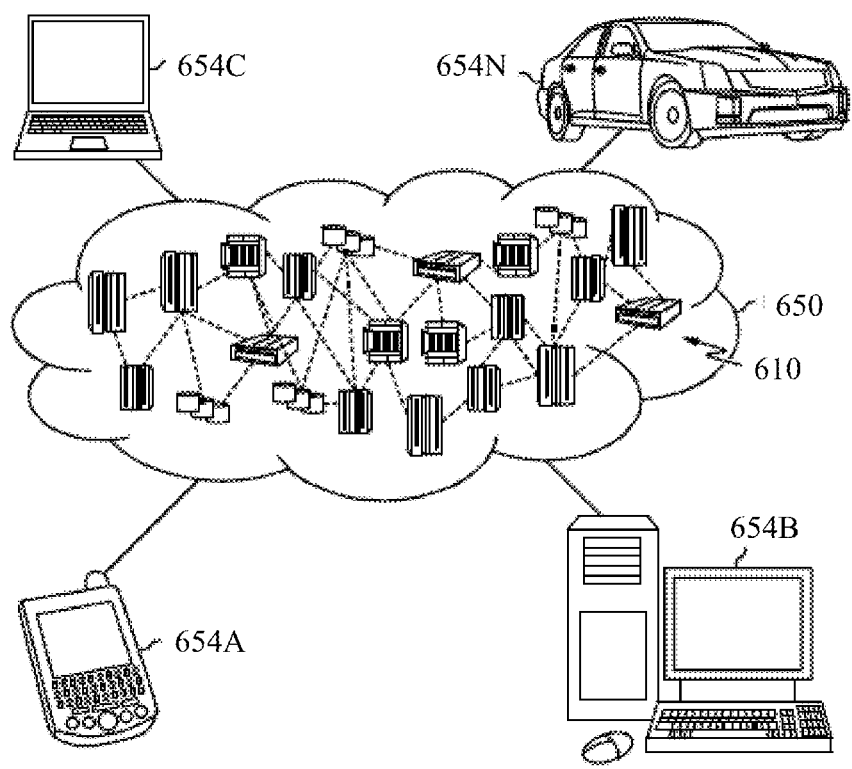
FIG. 6 depicts a cloud computing environment in accordance with one or more embodiments described herein.

Referring now to FIG. 6, an illustrative cloud computing environment 650 is depicted. As shown, cloud computing environment 650 includes one or more cloud computing nodes 610 with which local computing devices used by cloud consumers, such as, for example, personal digital assistant (PDA) or cellular telephone 654A, desktop computer 654B, laptop computer 654C, and/or automobile computer system 654N may communicate. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
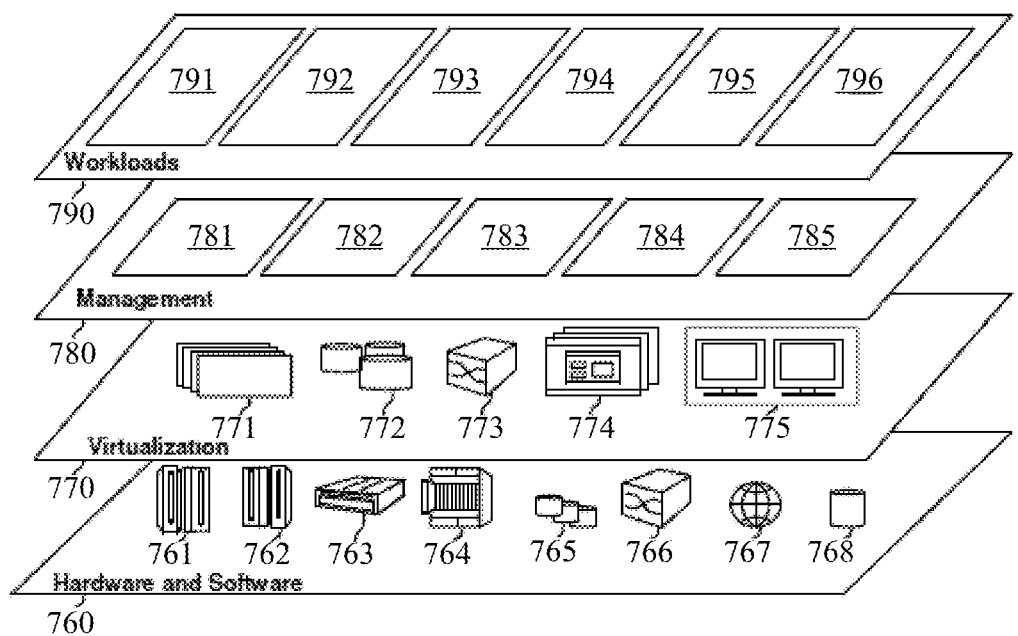
FIG. 7 depicts abstraction model layers in accordance with one or more embodiments described herein.

Referring now to FIG. 7, a set of functional abstraction layers provided by cloud computing environment 650 (FIG. 6) is shown. Repetitive description of like elements employed in other embodiments described herein is omitted for sake of brevity. It should be understood in advance that the components, layers, and functions shown in FIG. 7 are intended to be illustrative only and embodiments of the disclosure are not limited thereto. As depicted, the following layers and corresponding functions are provided. Repetitive description of like elements employed in other embodiments described herein is omitted for sake of brevity.

Hardware and software layer 760 includes hardware and software components. Examples of hardware components include: mainframes 761; RISC (Reduced Instruction Set Computer) architecture-based servers 762; servers 763; blade servers 764; storage devices 765; and networks and networking components 766. In some embodiments, software components include network application server software 767 and database software 768.

Virtualization layer 770 provides an abstraction layer from which the following examples of virtual entities may be provided: virtual servers 771; virtual storage 772; virtual networks 773, including virtual private networks; virtual applications and operating systems 774; and virtual clients 775.

In one example, management layer 780 may provide the functions described below. Resource provisioning 781 provides dynamic procurement of computing resources and other resources that are utilized to perform tasks within the cloud computing environment. Metering and Pricing 782 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 783 provides access to the cloud computing environment for consumers and system administrators. Service level management 784 provides cloud computing resource allocation and management such that required service levels are met. Service Level Agreement (SLA) planning and fulfillment 785 provide pre-arrangement for, and procurement of, cloud computing resources for which a future requirement is anticipated in accordance with an SLA.

Workloads layer 790 provides examples of functionality for which the cloud computing environment may be utilized. Examples of workloads and functions which may be provided from this layer include: mapping and navigation 791; software development and lifecycle management 792; virtual classroom education delivery 793; data analytics processing 794; transaction processing 795; and therapy and/or medicine prescription updating 796. Various embodiments of the present disclosure can utilize the cloud computing environment described with reference to FIGS. 6 and 7 to determine a therapy for pain management and reduction as described herein.

The computer processing systems, computer-implemented methods, apparatus and/or computer program products employ hardware and/or software to solve problems that are highly technical in nature (e.g., updating and applying a pain treatment in real-time based on one or more analytically computed pain perception values that can characterize one or more pain associated with a user), that are not abstract and cannot be performed as a set of mental acts by a human. For example, an individual, or even a plurality of individuals, cannot readily collect, maintain, and/or analyze vast volumes of data as expeditiously and/or efficiently as the various embodiments described herein. Additionally, one or more embodiments described herein can utilize AI technologies that are autonomous in their nature to facilitate determinations and/or predictions that cannot be readily performed by a human.

The present disclosure may include a system, a method, and/or a computer program product at any possible technical detail level of integration. The computer program product may include a computer readable storage medium (or media) having computer readable program instructions thereon for causing a processor to carry out embodiments of the present disclosure. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, to perform embodiments of the present disclosure.

Embodiments of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement embodiments of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present disclosure. In this regard, each block in the flowchart or block diagrams may represent a component, segment, or portion of instructions, which comprises one or more executable instructions for implementing the specified logical function(s). In some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program components. Generally, program components include routines, programs, components, data structures, etc. that perform tasks and/or implement abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated embodiments can also be practiced in distributed computing environments where tasks are performed by remote processing devices that are linked through a communications network. However, some, if not all embodiments of this disclosure can be practiced on stand-alone computers. In a distributed computing environment, program components can be in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other embodiments or designs, nor is it meant to preclude equivalent exemplary structures and techniques known to those of ordinary skill in the art.

As it is employed in the subject specification, the term "processor" can refer to substantially any computing processing component or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, to optimize space usage or enhance performance of user equipment. A processor can also be implemented as a combination of computing processing components. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random-access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
 a memory that stores computer executable components;
 a processor, operably coupled to the memory, and that executes the computer executable components stored in the memory, wherein the computer executable components comprise:
  a data collection component that determines, using one or more sensors, parameter data associated with a subject over a period of time, wherein the parameter data comprises psychological data comprising at least one psychological parameter associated with the subject, physiological data comprising at least one physiological parameter associated with the subject, behavior data comprising activities performed by the subject, treatment data comprising a group of treatments applied to the subject, and timing data comprising times associated with the parameter data;
  a computing component that, using a machine learning model iteratively during the period of time:

determines pain perception data representative of pain perception of the subject at the times based on the psychological data and the physiological data, learns relationships between the psychological data, the physiological data, the behavior data, the treatment data, the pain perception data, and the timing data, and generates, based on the learned relationships, an optimal treatment comprising one or more combinations of treatments from the group of treatments, and timings for administration of the one or more combinations of treatments to reduce the pain perception of the subject; and a treatment component that controls a device associated with the subject to administer at least a portion of the optimal treatment to the subject.

2. The system of claim 1, wherein the parameter data further comprises environmental data comprising at least one environmental parameter associated with the subject.

3. The system of claim 2 where the learned relationships are further based on the environmental data.

4. The system of claim 1, wherein the group of treatments comprise at least one of a medication, a wearable device, or a procedure.

5. The system of claim 1, further comprising a communication component that:

presents the optimal treatment as a suggestion to the subject via an interface that enables the subject to evaluate an effectiveness of the optimal treatment, and receives input from the subject indicating whether the subject approves the optimal treatment.

6. The system of claim 1, wherein the treatment component comprises causes the device associated with the subject to apply at least the portion of the optimal treatment without input from the subject for improved processing efficiency.

7. The system of claim 1, wherein the computing component modifies, using the machine learning model, the optimal treatment based on feedback from the subject.

8. A computer-implemented method, comprising:

determining, by a system operatively coupled to a processor, using one or more sensors, parameter data associated with a subject over a period of time, wherein the parameter data comprises psychological data comprising at least one psychological parameter associated with the subject, physiological data comprising at least one physiological parameter associated with the subject, behavior data comprising activities performed by the subject, treatment data comprising a group of treatments applied to the subject, and timing data comprising times associated with the parameter data; and iteratively during the period of time:

determining, by the system, using a machine learning model, pain perception data representative of pain perception of the subject at the times based on the psychological data and the physiological data;

learning, by the system, using the machine learning model, relationships between the psychological data, the physiological data, the behavior data, the treatment data, the pain perception data, and the timing data;

generating, by the system, using the machine learning model, based on the learned relationships, an optimal treatment comprising one or more combinations of treatments from the group of treatments, and timings for administration of the one or more combinations of treatments to reduce the pain perception of the subject; and controlling, by the system, a device associated with the subject to administer at least a portion of the optimal treatment to the subject.

9. The computer-implemented method of claim 8, wherein the parameter data further comprises environmental data comprising at least one environmental parameter associated with the subject.

10. The computer-implemented method of claim 9, wherein the learned relationships are further based on the environmental data.

11. The computer-implemented method of claim 8, wherein the group of treatments comprise at least one of a medication, a wearable device, or a procedure.

12. The computer-implemented method of claim 8, further comprising:

presenting, by the system, the optimal treatment as a suggestion to the subject via an interface that enables the subject to evaluate an effectiveness of the optimal treatment, and receiving, by the system, input from the subject indicating whether the subject approves the optimal treatment.

13. The computer-implemented method of claim 8, wherein the controlling the device associated with the subject to administer at least the portion of the optimal treatment to the subject occurs without input from the subject.

14. The computer-implemented method of claim 8, further comprising modifying, by the system, using the machine learning model, the optimal treatment based on feedback from the subject.

15. A computer program product for providing pain management comprising a computer readable storage medium having program instructions embodied therewith, the program instructions executable by a processor to cause the processor to:

determine, using one or more sensors, parameter data associated with a subject over a period of time, wherein the parameter data comprises psychological data comprising at least one psychological parameter associated with the subject, physiological data comprising at least one physiological parameter associated with the subject, behavior data comprising activities performed by the subject, treatment data comprising a group of treatments applied to the subject, and timing data comprising times associated with the parameter data;

iteratively during the period of time:

determine, using a machine learning model, pain perception data representative of pain perception of the subject at the times based on the psychological data and the physiological data;

learning, using the machine learning model, relationships between the psychological data, the physiological data, the behavior data, the treatment data, the pain perception data, and the timing data;

generate, using the machine learning model, based on the learned relationships, an optimal treatment comprising one or more combinations of treatments from the group of treatments, and timings for administration of the one or more combinations of treatments to reduce the pain perception of the subject; and control a device associated with the subject to administer at least a portion of the optimal treatment to the subject.

16. The computer program product of claim 15, wherein the parameter data further comprises environmental data comprising at least one environmental parameter associated with the subject.

17. The computer program product of claim 16, wherein the learned relationships are further based on the environmental data.

18. The computer program product of claim 15, wherein group of treatments comprise at least one of a medication, a wearable device, or a procedure.

19. The computer program product of claim 15, wherein the program instructions further cause the processor to:
   present the optimal treatment as a suggestion to the subject via an interface that enables the subject to evaluate an effectiveness of the optimal treatment, and
   receive input from the subject indicating whether the subject approves the optimal treatment.

20. The computer program product of claim 15, wherein the controlling the device associated with the subject to administer at least the portion of the optimal treatment to the subject occurs without input from the subject.

* * * * *